United States Patent
Teiwes et al.

(10) Patent No.: US 7,480,396 B2
(45) Date of Patent: Jan. 20, 2009

(54) MULTIDIMENSIONAL EYE TRACKING AND POSITION MEASUREMENT SYSTEM FOR DIAGNOSIS AND TREATMENT OF THE EYE

(75) Inventors: Winfried Teiwes, Teltow (DE); Horia Grecu, Teltow (DE)

(73) Assignee: Sensomotoric Insturments GmbH (DE)

( * ) Notice: Subject to any disclaimer, the term of this patent is extended or adjusted under 35 U.S.C. 154(b) by 776 days.

(21) Appl. No.: 10/630,001

(22) Filed: Jul. 29, 2003

(65) Prior Publication Data
US 2005/0024586 A1 Feb. 3, 2005

(51) Int. Cl.
*G06K 9/00* (2006.01)
(52) U.S. Cl. .................. 382/117; 382/103; 351/206; 351/208; 351/209; 351/240
(58) Field of Classification Search .......... 351/206, 351/208, 209, 240; 382/103, 117; 348/78
See application file for complete search history.

(56) References Cited

U.S. PATENT DOCUMENTS

| | | | | | |
|---|---|---|---|---|---|
| 5,098,426 | A | * | 3/1992 | Sklar et al. | 606/5 |
| 5,311,879 | A | * | 5/1994 | Yamada et al. | 600/558 |
| 6,322,216 | B1 | * | 11/2001 | Yee et al. | 351/210 |

* cited by examiner

*Primary Examiner*—Matthew C Bella
*Assistant Examiner*—John B Strege
(74) *Attorney, Agent, or Firm*—Stevens Law Group

(57) ABSTRACT

The present invention relates to improved ophthalmic diagnostic measurement or treatment methods or devices, that make use of a combination of a high speed eye tracking device, measuring fast translation or saccadic motion of the eye, and an eye position measurement device, determining multiple dimensions of eye position or other components of eye, relative to an ophthalmic diagnostic or treatment instrument.

15 Claims, 32 Drawing Sheets

Figure 1
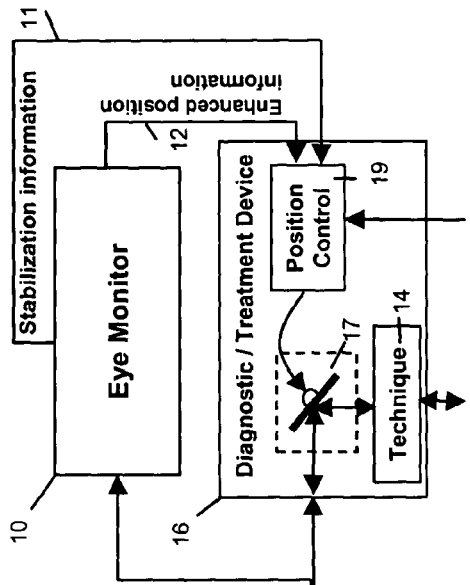
Fig. 1b
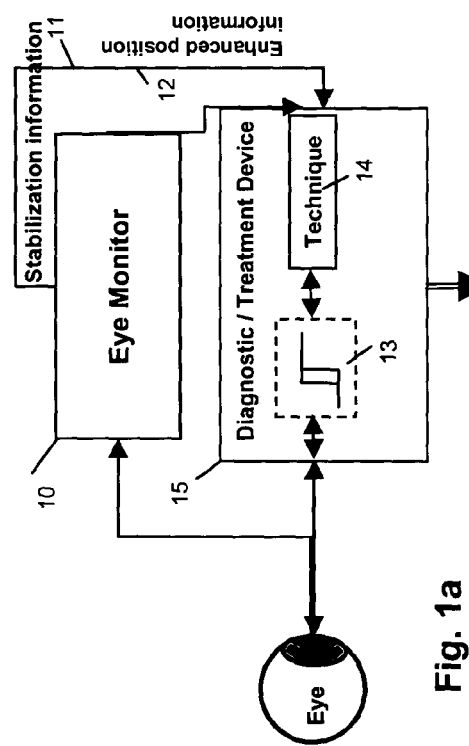
Fig. 1a
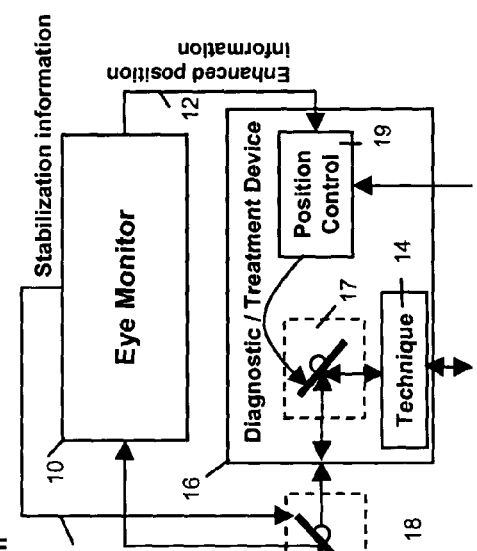
Fig. 1c

Figure 14
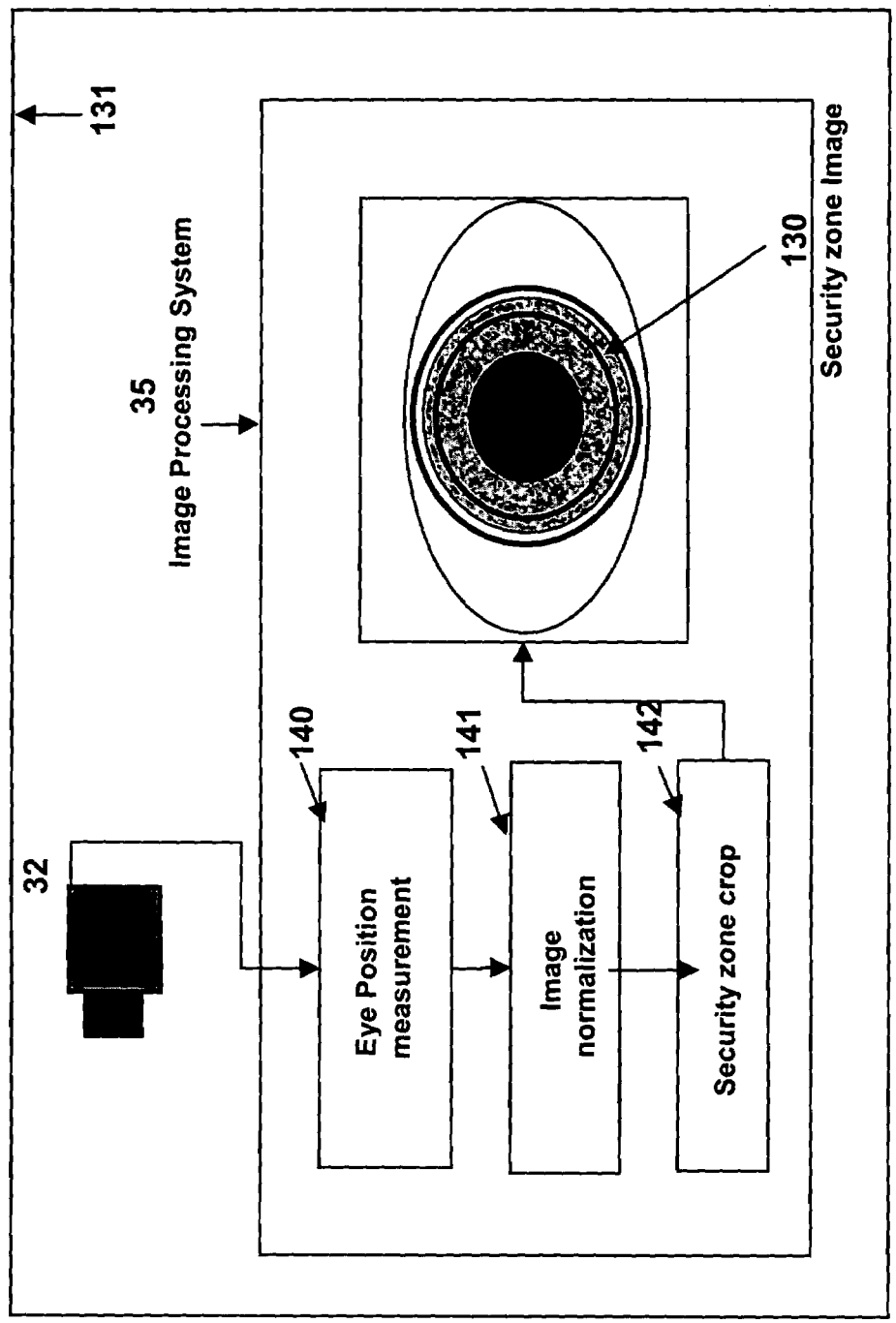
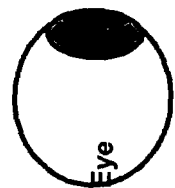

Figur 17

Figure 22
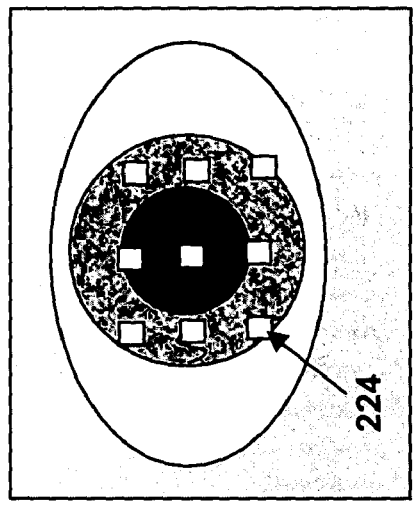
Fig. 22b:
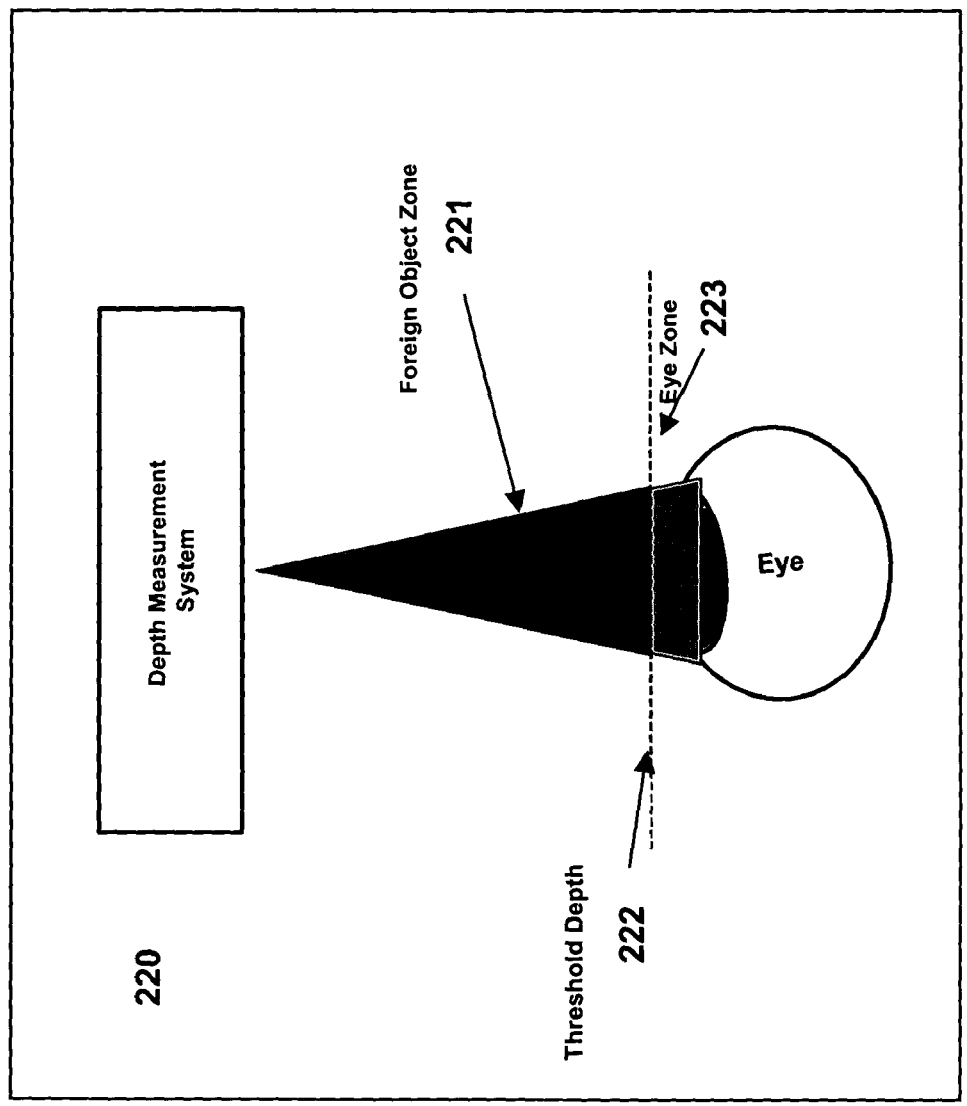
Fig. 22a:

MULTIDIMENSIONAL EYE TRACKING AND POSITION MEASUREMENT SYSTEM FOR DIAGNOSIS AND TREATMENT OF THE EYE

The present application is a regular patent application of, and claims the benefit of priority from, the following U.S. Provisional patent applications
  (1) U.S. Provisional Patent Application Ser. No. 60/267,931 filed Feb. 9, 2001
    Method and apparatus for tracking translations and rotations of the eye in 6 dimensions in laser refractive surgery; Huppertz et al.,
  (2) U.S. Provisional Patent Application Ser. No. 60/277,309 filed Mar. 20, 2001
    Method and Apparatus for real time, dynamic measurement of corneal distance and pachymetry using eye tracking and optical coherence tomography; Ralf Weise, Winfried Teiwes, Eberhard Schmidt
  (3) U.S. Provisional Patent Application Ser. No. 60/350,684 filed Nov. 13, 2001
    Method and apparatus for measuring eye movements and combining it with different eye tracking technologies in order to maintain a fast, robust, accurate, and absolute eye position during treatment or diagnosis of the eye; Teiwes et al.,
It also claims the benefit of priority from the following International patent application
  (4) International Patent Application #PCT/EP02/01413 filed Feb. 11, 2002
    Multidimensional Eye Tracking and Position Measurement System for Diagnosis and Treatment of the Eye; Teiwes et al.,
the full disclosure of which is incorporated herein by reference.

FIELD OF THE INVENTION

The present invention relates to improved ophthalmic diagnostic measurement or treatment methods or devices, that make use of a combination of a high speed eye tracking device, measuring fast translation or saccadic motion of the eye, and an eye position measurement device, determining multiple dimensions of eye position or other components of eye, relative to an ophthalmic diagnostic or treatment instrument.

In particular, the invention relates to systems for diagnosis and/or treatment of the eye, and more particularly where the eye can move during the diagnostic and/or treatment procedure.

BACKGROUND OF THE INVENTION

The present invention is generally related to measurement of eye movements, and in particular embodiments provides methods, systems, and devices for measuring the position of the eye relative to diagnostic devices and/or treatment devices such as laser systems for refractive surgery of the cornea or other parts of the eye.

Ophthalmic diagnostic devices, such as Topography, Pachymetry, Optical Coherence Topography (OCT) and Wavefront sensing systems measure the shape, thickness and optical parameters of different surfaces of the eye. With the advances in methods, systems and devices in the ophthalmic diagnosis an accurate measurement of the exact location of each diagnostic measurement on the eye is highly desired in order to combine, compare or map succeeding measurements with the same or different devices over time together. Some techniques, such as OCT provide only one measurement (i.e. distance and thickness of the cornea) at a specific location on the eye at a time. In order to allow an assessment over a specific section (line) or are area, several measurements are taken consecutively at different locations on the eye over a certain period of time by scanning the diagnostic measurement device over the eye.

Ophthalmic treatment devices, here in more specific laser systems, perform treatments on different surfaces of the eye (i.e. cornea, lens, iris or retina). In refractive surgery, laser systems are used to achieve a desired change in corneal shape, with the laser removing thin layers of corneal tissue at specific locations on the cornea using a technique generally described as ablative photodecomposition. Laser eye surgeries are useful in procedures such as photorefractive keratectomy, phototherapeutic keratectomy, laser in situ keratomileusis (LASIK), and the like. Newer Femto-second laser systems perform specific procedures on the cornea to create flap on the cornea or perform direct treatment with the corneal material. Laser treatment procedures require several specific ablations at a defined position on the eye over the treatment time to create the intended result. The laser may or may not be directed towards different locations onto the eye and the laser beam may be modified in size, form (i.e. slit, circular) and energy profile throughout the ablation procedure.

To position a diagnostic measurement or treatment procedure onto the eye, the location of the eye needs to be known. The eye position may therefore be adjusted according to the instrumentation to align the eye in a defined position relative to the optical axis of the diagnostic or treatment system. During the procedure, which may take seconds or minutes, the patients eye or head can move the away from this initial aligned position. Therefore, the ability to automatically track or follow the eye position throughout the diagnostic or treatment procedure is recognized as a highly desirable, if not a necessary feature within these systems.

Movements of the eye include voluntary and involuntary—primarily rotational—movement of the eye in the head. Even if the patient is cooperative and can sharply visualize and fixate on a specific fixation target, certain eye movement will still occur, such as eye rotation in yaw (horizontal), pitch (vertical) and roll (torsion). Head motion can also occur during the treatment, resulting primarily into a horizontal and vertical translational movement relative to—and rotational movement around—the optical axis of the diagnostic or treatment system. In specific treatment procedures, such as treatment of irregular astigmatism or cutting the flap with a femtosecond laser system the absolute translational and rotational position of the eye in all six dimensions is required relative to the treatment system for accurate and secure treatment.

Therefore, tracking the eye has been proposed to avoid uncomfortable structures, which attempts to achieve total immobilization of the eye and locate the eye at a defined position relative to the diagnostic or treatment device. A variety of structures and techniques have been proposed for tracking the eye during the diagnosis and/or treatment, and to position the diagnostic measurement or treatment position to a certain position on the eye. For this purpose a sensor device fixed relative to the diagnostic or treatment system observes the eye or its specific features. Two different general approaches, Closed-loop and Open-loop tracking Eye Tracking Methods have been introduced.

Closed-Loop Eye Tracking Methods provide a horizontal and vertical stabilization of an optical projection of the eye towards the diagnostic or treatment system. Movements of the eye are sensed by means of detecting one or multiple specific feature of the eye (i.e. mostly a specific section of the pupil iris boundary is used) with a sensor device via a position controllable x-y mirror device. The sensor provides an position error signal if the tracked feature of the eye is moved, which is then used by a controller to create a feedback positioning signal to control an x-y mirror position to project the tracked feature back onto the same location on the sensor device. This technique is also called closed loop tracking and performs a stabilization of the target relative to the sensor. If the sensor device is mounted fixed to the diagnostic and treatment device, the projected image of the eye is stabilized relative to the diagnostic or treatment device. The sensor with its applied method senses a deviation of the projected eye from its indented stabilized position and controls the mirror to project the eye back into the intended stabilized position. A measurement of the actual x and y position may be obtained indirectly from the control output positioning the x-y mirror device.

One specific implementation of these Closed-loop Eye Tracking Methods is described in the patent U.S. Pat. No. 5,632,742 (Eye Movement Sensing Method and System, Frey et al.), hereafter called LADAR tracker, which applies through an motorized x/y mirror device sequentially 4 light spots onto 4 different locations of the pupil-iris boundary, and measures the returned light from each location. Eye motion relative to the light spots result into a change of brightness returned by each spot caused by different light energy reflected by iris and pupil. This analysis of the returned light intensity by each of the four spots provides an error position signal used to control the motorized x-y mirror position to reposition the spots centered on the pupil-iris boundary. As a result the x-y mirrors are always in a fixed orientation relative to the pupil-iris boundary, which the laser treatment device can now use to project its ablation laser spot stabilized onto the eye. A relative positioning of the treatment location onto different locations onto the eye can be accomplished using a second set of controllable mirrors. Limiting the analysis of the eye to the intensity of light returned from 4 small discrete areas of the eye, allows fast processing and positioning of the mirrors, to stabilize the projection of the eye for treatment even during fast eye movements.

To initiate the tracking with this technique the pupil size needs to be known to adjust the relative position of the spots onto the pupil-iris boundary, which requires manual or semi-automatic adjustment procedures. Furthermore, the pupil size needs to be constant throughout the procedure, since the light spots projected onto the pupil-iris boundary are fixed relative to each other. However, pupil size changes generally occur and therefore need to be omitted as much as possible by dilating the pupil pharmaceutically before the treatment. This requires another treatment step in the overall procedure and creates uncomfortable temporary side effects for the patient (less visual acuity during the dilation period) and can influence the clinical outcome of the diagnostic or treatment procedure. Firstly, widening the pupil—the target to be tracked—is not symmetrical relative to any fixed point on the cornea—the target to be treated—and therefore a positioning error may occur. This may be compensated with a specific calibration procedure. Secondly, dilation may change physical characteristics of the eye, which then may affect the treatment process (i.e. cutting the flap) itself.

Another technique of Closed-loop Eye Tracking Methods combines the optical technique of Confocal Reflectometry with the electronic technique of phase-sensitive detection, hereafter called CRP Tracker, as described in the patent U.S. Pat. No. 5,943,115. It utilizes a high-bandwidth feedback signal derived from the light of a low-power "tracking beam" scattered off the surface of the tracked object (i.e. retina or iris of the eye). The tracking beam is directed onto the tracked surface of the eye by fast x-y position controlled tracking mirrors. The feedback signal continually adjusts the mirror orientations to lock the tracking beam to a target on the tracked surface of the object and the tracking mirror surfaces follow the motion of the tracked surface of the object. The diagnostic or treatment device may therefore be applied fixed to the eye through the tracking mirrors. Relative positioning of a diagnostic or treatment location onto different location onto the eye can then be accomplished using a second set of controllable mirrors.

One benefit of the CRP tracker is, that it tracks only a single small target area, which provides sufficient contrast changes, i.e. a specific area of the iris or retina. This eliminates the need of relative positioning of several areas and compensation of distances during the procedure as need with the LADAR tracker. Although the CRP tracker has been primarily applied for tracking of retinal features for diagnosis and/or treatments of the retinal surface, this technique may be applied to track a feature close to the surface to be diagnosed or treated. As with the LADAR tracker, this technique provides no automated method to identify which feature on which surface shall be tracked. In addition, there is no objective control available that a specific feature is lost or another similar feature clos by is tracked, which would result into a position error.

The above-described Closed-loop Eye Tracking Methods provide a fast two dimensional tracking and stabilization of the projected eye to the diagnostic or treatment device. However, the tracking of the eye is performed on only specific features undergoing both translational and rotational movement of the eye. These methods cannot discriminate between translational and rotational movement of the eye, which is becoming recently of more interest. Furthermore, the distance of the eye relative to the diagnostic and/or treatment device is not measured and torsional rotations of the eye are either not detected (LADAR tracker) or may create an error in horizontal and vertical tracking (CRP tracker). Furthermore, the introduction of other objects into the field of view such as surgical instruments occluding the tracked featured may create a false measurement or loss of tracking.

Open-Loop Eye Tracking Methods sense the eye directly or via a fixed mirror system, and process the sensor information to identify a specific feature and its location in the sensor information.

The most common approach of Open-Loop Eye Tracking Methods, hereafter called VIDEO tracker, uses imaging devices, i.e. a CCD camera, which is mounted in such a way that it observes the eye within the optical axis of the diagnostic or treatment device. The eye is illuminated with infrared light from light sources which are mounted non-coaxial from the optical-axis. Using infrared filters the imaging device integrates an image of the eye from the infrared light, which provides a higher image contrast between the dark pupil and surrounding iris and sclera than with other visible light. The obtained images are transferred to an image processing system where each image is digitized in picture elements (pixels) and processed to determine the center of the pupil. In these systems the pupil is detected as a circular formed dark area within an otherwise brighter image of the eye from the iris and sclera. Detection of the pupil area is performed using a brightness threshold to detect all pixels, which are below this threshold. Thereafter, all pixels may be analyzed for horizontal and vertical connectivity to other pixels, which are below this threshold, resulting in an identification of several objects containing connected pixel elements, which are below this threshold level. All objects are thereafter analyzed according to several geometric parameters to identify the pupil. If an object in the image fulfils all these geometric requirements for a pupil, the center of gravity (COG) or other geometric calculations are preformed to obtain a center position from this pupil object.

The obtained horizontal and vertical pupil position relative to the optical axis is provided to the diagnostic and/or treatment system as horizontal and vertical position of the eye during the procedure. This information is then used in different ways, depending on the requirements from the diagnostic and/or treatment procedure, ranging from only registering where a diagnostic measurement or treatment was performed on the eye, performing a diagnostic measurement or treatment only within a certain position range of the eye, or offsetting the diagnostic measurement and/or treatment position with the eye position using a x/y mirror system. The latter case is often used for example in scanning laser system, where the eye position is used to offset to the indented scanning position of the treatment.

An improvement towards the above-described VIDEO tracker has been proposed in Patent U.S. Pat. No. 6,322,216, where 2 off axis imaging devices are used to overcome challenges integrating the imaging devices within the optical path. The images of each imaging device may be used to determine the overall horizontal and vertical position of the eye from the perspective of each camera. However, due to the off-axis viewing of the eye, a change of eye distance relative to the laser system—even along the optical z axis with no change of horizontal and vertical position—results in a different horizontal and vertical position measurement obtained by each off axis imaging device. To overcome this limitation the position obtained from both imaging devices must be combined in order to determine also the distance of the eye relative to the laser device, allowing a means of correcting the parallax error and providing a correct horizontal and vertical position of the relative to the treatment device. Therefore, if depth changes of the eye relative to the treatment device can occur, always the image analysis of both imaging devices is needed for an accurate measurement of horizontal and vertical position.

VIDEO trackers have been proven effective for several applications in diagnostic and/or treatment applications. In the field of refractive surgery, VIDEO trackers currently have several advantages and limitations compared with the other Eye Tracking Methods. An advantage of the VIDEO tracker over the LADAR tracker is, that VIDEO tracker can track the pupil at different sizes of the pupil. This advantage however has a certain limitation, since pupil size changes do not occur symmetrically relative to the cornea, which may creates a positioning error on the cornea at different pupil sizes. The setup of video trackers is simpler and can be automatic, however the speed of the VIDEO tracker is limited to the image rate of the sensors and the processing of the image. More specifically, the time needed to integrate an image on the sensor, to transfer the sensor information to the processing unit, and to process the image to obtain the pupil position information, results in a latency of position information within which the eye may continue to move, resulting in a dynamic positioning error of a succeeding diagnosis or treatment. This latency has been minimized using faster image sensors with faster image rates to have approximately the same overall latency period as with the LADAR tracker.

Although the known Eye Tracking devices have proven effective and safe for the current state of art in diagnostic or treatment of the eye, recent improvements and developments in ophthalmic diagnostic and/or treatment devices as well as the procedures involved using this technology have an increased demand on resolution, accuracy, dimensions, robustness and security for the registration of eye position and to control for it change during the procedure. This demand cannot be fulfilled by the current Eye Tracking Methods, primarily limited by its overall simplified measurement of a "projected" pupil based position onto a sensor device and not taking into account the different translational or rotational state of the eye in space relative to the diagnostic and/or treatment device.

BRIEF DESCRIPTION OF THE DRAWINGS

FIG. 1 is an overview of typical system integrations of the invented Eye Monitor with diagnostic and/or treatment devices.

FIG. 14 shows in greater detail the security zone image acquisition component from FIG. 13.

FIGS. 22a and 22b show how foreign objects an be detected using range segmentation.

SUMMARY OF THE INVENTION

Figure 2:
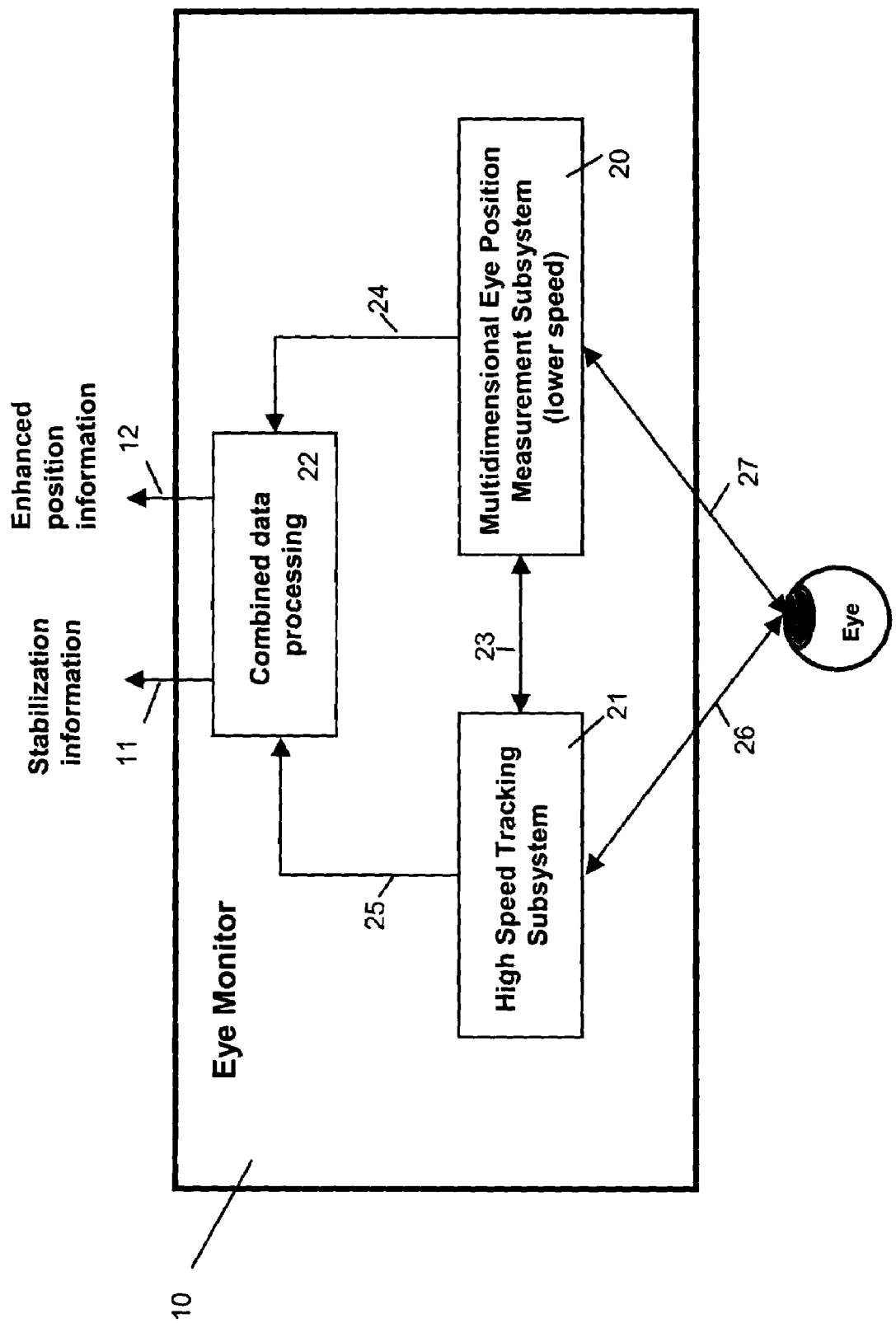
FIG. 2 provides overall block diagram of the Eye Monitor, including the High Speed Tracking Subsystem and the Multidimensional Eye Position Measurement Subsystem

The present invention proposes improved diagnostic and/or treatment of the eye such as with laser surgery and/or eye tracking systems, methods and devices.

To improve the resolution of diagnostic and/or treatment of the eye a higher positioning accuracy is proposed by measuring more dimensions of eye position than just tracking the eye horizontal and vertical projection of the eye and its distance position with previously described systems and methods. The proposed advanced eye tracking system, hereafter called Eye Monitor, provides a multidimensional eye position measurement independent of pupil size changes and takes into account that iris landmarks are not always be visible in the diagnostic and/or treatment procedure. Translational movement of the eye are separately determined to provide a true rotation measurement of the eye relative to the diagnostic and/or treatment device in terms if pitch (vertical rotation), and yaw (horizontal rotation) and roll (torsional rotation) position of the eye. Furthermore, a measurement of the distance (depth) of the eye relative to the diagnostic and/or treatment device and measurement of thickness of specific materials such as the cornea can be provided. Foreign objects, such as surgical instruments need to be securely identified to prevent these instruments obstructing the surgical or measuring beam and therefore reducing the effectiveness of the correction or measurement.

In addition to the improved static accuracy, the accuracy during dynamic movement of the eye is improved through a combination of the above advanced Eye Position Measurement System with a High Speed Tracking system. The system proposed supports stabilized (closed-loop) and non-stabilized (open-loop) embodiments. In addition, automatic adjustment and calibration procedures for user-friendly and service-friendly maintenance of the above specifications are proposed.

To fulfill these requirements this invention proposes an advanced eye tracking system and multidimensional eye position measurement system and method to be integrated into the diagnostic and/or treatment systems for the eye.

The invention proposes an advanced Eye Monitor 10 providing fast eye tracking information for stabilization 11 and enhanced eye positioning information 12 which can be integrated in different ways with diagnostic and/or treatment devices 15 and 16 as shown in FIG. 1. Diagnostic and/or treatment devices consist of a technique 14 to perform either: a diagnostic measurement of the eye like Topography, Wavefront, Pachymetry, Optical Coherence Tomography; or a treatment technique to treat the eye at the cornea or other surfaces of the eye such as with refractive laser systems, or combination of diagnostic and treatment technique such as a refractive laser together with a diagnostic method such as Pachymetry or Topography or others, to provide a diagnostic measurement during the treatment.

Some diagnostic and/or treatment devices—as shown in FIG. 1a—perform a measurement or treatment at a fixed location or area relative to this optical axis. Here the information from the Eye Monitor can be used to limit the measurement or treatment range to a certain range of eye position relative to the device, either electrically or optically with 13 or to register the location where a certain diagnostic measurement or treatment was performed on the eye.

Other devices—as shown in FIGS. 1b and 1c—provide also means to position the diagnostic measurement or treatment at different locations onto the eye using a x/y position controllable device 17, i.e. a x-y scanning mirror. In these devices the information 11 and 12 from the Eye Monitor can be used—in addition to the functions described for systems in FIG. 1a—to offset the intended diagnostic or treatment location relative to the eye with the eye position in the position control module 19. With the information from the Eye Monitor the position may be corrected not only for horizontal and vertical movement, but also taking into account the enhanced degrees of eye movements such as torsional position changes or rotation and translation of the eye, changes in pupil center position relative to the eye due to pupil dilation, parallax errors due to tracking of features at different depth and position of the eye relative to other instruments, which may hinder treatment or diagnosis, such as those detected using foreign object detection techniques.

Some diagnostic and or treatment devices, for example refractive laser treatment devices, require a high dynamic accuracy during fast eye movements which occur primarily during horizontal (yaw) and vertical (pitch) rotations of the eye during saccades. For this purpose, the faster available tracking information 11 can be used to control an additional position controllable mirror 18—as shown in FIG. 1c—to stabilize the projection of the eye as seen by the diagnostic/treatment device 16 through this mirror 18. This eliminates complex synchronization aspects of the Eye Monitor 10 with the diagnostic and/or treatment device 16, while still providing high dynamic position accuracy for relevant fast eye movements. Slower positional changes such as center shifts due to pupil size changes or other rotational movements of the eye provided from the Eye Monitor as enhanced position information 12, can still be corrected with the position control module 19 and position controllable mirror system 17 of the diagnostic/treatment device.

The Eye Monitor 10 proposed by this invention consists of several subsystems as shown in FIG. 2. A first subsystem, the High Speed Tracking Sub-System 21, tracks fast translational motion or saccadic motion of the eye by tracking a specific feature of the eye. The second subsystem, 20, performs a multidimensional eye position measurement, which determines accurately the location and orientation of the eye as well as specific features of the eye relative to the diagnostic and/or treatment device using different image processing methods normally at a lower speed. A further subsystem, 22 combines the measurements of the two systems for obtaining a multiple dimensional model of the eye position that is more accurate than the model obtainable from either system individually.

The Multidimensional Eye Position Measurement Subsystem makes use of one imaging device aligned coaxially with the optical axis of the diagnostic and/or treatment system. The images obtained are processed with specific image processing methods to obtain multiple degrees of freedom of eye position relative the diagnostic and/or treatment device with enhanced accuracy. An enhanced, optionally structured illumination and optical filtering facilitates the imaging of a high contrast image of the relevant features of the eye. These images are then processed by these specific image processing methods to obtain horizontal and vertical measurement of eye position based on both pupil center and limbus boundary, or other eye fixed features, to determine and correct for pupil center shift due to pupil size changes. Roll rotations of the eye relative to the diagnostic and treatment device are obtained by methods using iris features, blood vessels on the cornea and corneal markings applied to the eye including colored markings and surgical markings such as the borders of the flap cut. Differentiation of horizontal (x) and vertical (y) translational movements from pitch and yaw rotations of the eye can be determined by methods of determining head fixed features in addition to eye fixed features within the image. Furthermore a method is proposed to determine foreign objects introduced into the optical paths of diagnostic or surgery treatment for secure handling of diagnostic and/or treatment.

Optionally, one or multiple additional off-optical axis imagimaging devices, acquiring an image of the eye from an oblique angle, may be used by the slower Multidimensional Eye Position Measurement Subsystem to utilize methods for depth measurement on various locations of the eye by combining the results from different images with triangulation techniques. While the coaxial imaging device provides a measurement independent of depth changes the optional combination with the image of one off-axis imaging device provides a depth measurement. Depth based measurements of different locations of the eye can further be used for eye rotation estimation, and improved methods for depth based foreign object detection.

With an additional integration of a guiding beam (i.e. a guiding laser) within the optical path of the diagnostic and/or treatment device, which is visible also to the above described eye position measurement system, further methods are proposed to provide calibration of the coordinate systems from the eye position measurement system and diagnostic and/or treatment device as well as a method to register the diagnostic and or treatment position during normal operation with this Multidimensional Eye Position Measurement Subsystem.

For the High Speed Tracking Sub-System this invention proposes the use of different alternative techniques and methods.

The first approach is using a fast imaging device mounted coaxially with the optical path of the treatment device and providing a high contrast image of the pupil versus the iris using infrared illumination. The obtained images are transferred to an image processing system where each image is digitized and processed to determine the center of the pupil. Depending on the illumination used, the pupil is detected as a circular formed dark area within an otherwise brighter image of the eye from the iris and sclera, or alternatively a bright pupil against a darker iris. Hence, detection of the pupil area can be performed at high speed using a brightness threshold for detection of all pixels, which are below or alternatively above this threshold, analyzing their horizontal and vertical connectivity, and analyzing the resulting objects according geometric parameters to identify the pupil and its center either by computing the center of gravity (COG) or other geometric calculations such as circular fittings.

A second approach for high speed tracking is proposed by this invention using specific imaging devices which support selective readout out of lines or areas at higher speed than the full image. This allows higher frequency acquisition, faster transfer of relevant image information and faster processing. The selected area or lines can be positioned around the tracked object, i.e. the pupil, in the field of view of the image based on previous position information of the high speed tracking system or even from position information of the lower speed tracking system. This results in faster eye position determination at much lower latency than with the full image without losing significant spatial resolution and accuracy.

The above two imaging device based approaches for high speed tracking can be integrated with the Multidimensional Eye Position Measurement Subsystem described before, to obtain a more accurate model of eye position than is possible with one system alone. While the High Speed tracking system tracks for example fast eye movement using a high image rate or selective line readout and simple high contrast detection of the pupil center, the Multidimensional eye tracking systems determines at a slower rate pupil center shifts due to the slower pupil size changes and other dimensions of slower eye movement. The slower rate of center shift for example can be used by the high speed tracking system as a corrective offset for more accurate tracking between two slower—more complex—measurements.

One integration method for the high speed tracking system using an imaging device and the Eye Position Measurement system consists of one separate coaxial imaging device for each of the subsystems (i.e. one high resolution slower speed sensor and one higher speed imaging sensor) by dividing the optical path using a beam splitter or separate filtering of different illumination wavelengths (i.e. IR light for high speed tracking and visible light for Multidimensional Eye Position Measurement). Alternatively, a single high resolution imaging device can be used which supports also high image rate or selective line/area readout and slower speed eye position measurement. In this case every high speed image or the selected lines/areas is processed using the high speed tracking method. A sub-sampled full image from the same imaging device is used for the Multidimensional Eye Position Measurement System. A further integration is possible by using one or multiple off-axis mounted imaging devices with high image rate or selective line/area readout for the high speed processing system, and the coaxial high resolution imaging device for the Multidimensional Eye Position Measurement Subsystem.

As an alternative to imaging devices for high speed tracking of the eye, the use and integration of other non-image based eye tracking methods for high speed tracking with the Multidimensional Eye Position Measurement Subsystem is proposed by this invention.

Specifically, the integration of the fast non-image based LADAR tracking system combined with the imaging device based Eye Position Measurement system is proposed to overcome certain limitations of the LADAR tracker, such as the requirement for constant pupil size and providing a method to determine and correct for pupil center shifts due to pupil size changes. The LADAR tracker provides a fast pupil based tracking of the eye using a stabilization device. The Multidimensional Eye Position Measurement Subsystem may observe the eye either through the stabilized mirror or directly along the optical axis and provide a measurement of pupil size and an offset measurement of the pupil center due to pupil size changes by examining other landmarks on the eye with described methods (i.e. limbus features). The pupil size is measured with the imaging device based Eye Position Measurement system and is provided to the LADAR tracker to adjust its spacing of the spots tracked on the pupil/iris boundary. This allows the LADAR tracker to track fast eye movements even with different pupil sizes. Pupil size changes occur only at a lower speed, hence the pupil center shift obtained with the slower imaging device based Eye Position Measurement system is sufficient as a positioning offset to the laser positioning control system to offset the intended ablation position with the pupil center shift during the surgery. Similarly, other enhanced position information such as depth, torsional rotations may be used to correct the laser positioning of the treatment. The stabilized image of LADAR tracker may be used by the Multidimensional Eye Position Measurement Subsystem to image the eye at higher spatial resolution (less field of view is required since the measurement range is extended through the moving mirrors) and reducing the processing effort for several of the described methods. The combination of these systems allows accurate and very fast tracking of the eye with the LADAR tracker independent of pupil size and its change, and further dimensions and security measures provided from the Multidimensional Eye Position Measurement Subsystem.

A similar combination is proposed by this invention with the CRP trackers, where the image based measuring device provides the absolute orientation measurement relative to the CRP tracker and optionally also selective position to be used by the CRP tracker to track fast movements of the eye. The CRP tracking system provides a fast stabilization of the eye relative to the selected target on the eye.

Advanced diagnostic and/or treatment methods and procedures, such as Femto-second laser systems for refractive surgeries require a highly accurate distance measurement of the corneal surface relative to the laser device and its thickness at the current treatment location. For this purpose this invention includes—in addition to the eye tracking system—an optional integration of an Optical Coherence Tomography (OCT) system for enhanced depth and thickness measurement. The OCT measurement beam can be embedded coaxially with the optical axis of the diagnostic and/or treatment system and hence positioned with its position device to the intended location on the eye with the offset position of the eye from the eye tracking system. The OCT technique provides a measurement of the distance of the cornea and its thickness at this location on the eye. The diagnostic and/or treatment device may now record the depth and thickness measurement or control for example the focus of a Femto-second laser system to perform an appropriate ablation at the intended depth within the cornea using the distance and thickness information at this location. Repeating this procedure at different locations relative to the eye—stabilized by the eye tracker—provides a diagnostic measurement map without eye motion artifacts (i.e. to measure the thickness of the cornea either before a flap cut, to decide appropriate thickness of the cut or after the cut to determine residual thickness for secure treatments) or enables a secure intra-corneal treatment (i.e. cut a flap). For a stabilized embodiment the OCT beam may be embedded also through the stabilization mirror hence providing a measurement always at a fixed location on the eye.

DETAILED DESCRIPTION OF THE INVENTION

The general description of the Eye Monitor is described already in the summary of the invention as well as the functional overview of the subsystems of the Eye Monitor. In this section we will now describe first the Eye Position Measurement Subsystem and its overall integration into the Diagnostic and/or Treatment device, followed by the description of High Speed Tracking Subsystems and the joint integration with Eye Position Measurement Subsystem into the into the Diagnostic and/or Treatment device.

1 Eye Position Measurement Subsystem 1.1 Overview of System Components

Figure 3:
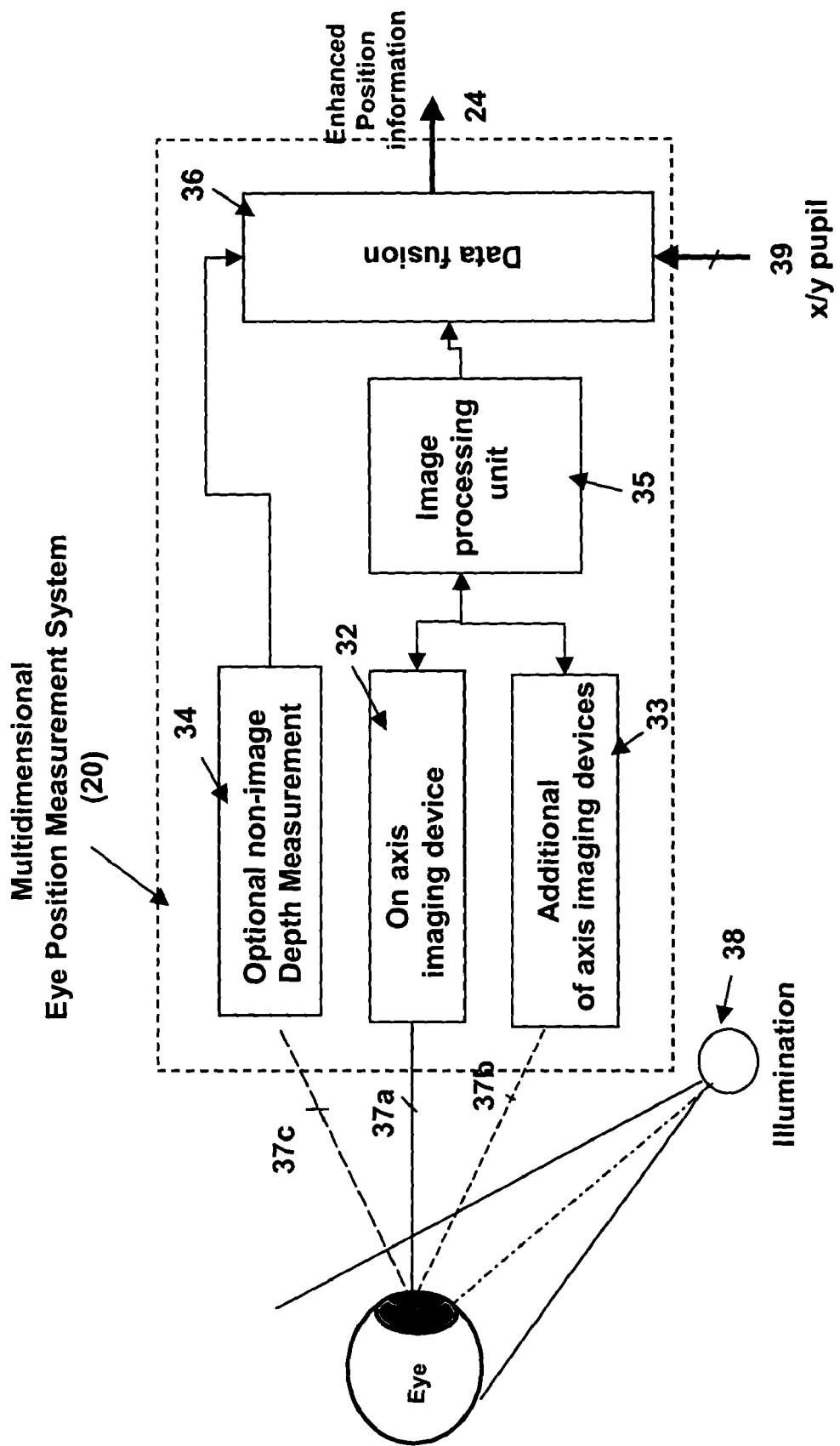
FIG. 3 is a block diagram of the multi-dimensional Eye Position Measurement System.

The Eye Position Measurement System is detailed in FIG. 3. It consists of one imaging device 32 (e.g. CCD, CMOS imaging devices) that observes the eye coaxially along the optical axis of the diagnostic and/or treatment device 37a. It provides means to determine various measurements like pupil and non-pupil based horizontal and vertical eye position measurement, torsional eye position (roll position around the visual axis of the eye), separated measurement of pitch rotation (vertical rotation) and yaw rotation (horizontal rotation) through additional registration of head translation, and foreign object detection.

Optionally, one or more additional imaging devices 33 are imaging the eye from an oblique position. The role of the additional module 33 is to allow enhanced measurements of eye position such as distance of the eye to the diagnostic and/or treatment device (depth) or determining the pitch and yaw rotation of the eye (tilt) by use of stereo imaging and triangulation methods. The optical path of system 33, referred symbolically as 37b, consist of one or more distinct optical paths that are usually off-axis with respect to optical axes 37a.

Another optional component 34, used in addition to either 32 or 32 & 33, provides an alternative non-image based measurement of a specific dimension, such as distance to specific surface (depth) or thickness between two distinct surfaces (thickness). Depth is defined here as eye position along the optical axes 37c used for integrating the 34 into the diagnostic and/or treatment device.

The image processing system 35 collects and analyses the consecutive images from imaging devices 32, 33. The image processing is performed by a number of algorithmic modules, each implemented as either a hardware or combined software & hardware solution. The modules can run in parallel or sequentially depending on the characteristics of the image processing hardware support. In a preferred embodiment the modules are implemented as a collection of software routines running on a dedicated image processing hardware platform and/or a PC system with a frame grabbing device. The system 35 outputs the measured position information to data fusion system 36 and can also send digital or analogical commands to the imaging devices 32, 33 to control the function of the imaging devices such as sampling rate, contrast, control of readout area, or optical adjustments. The data fusion system combines together the multidimensional measurements from module 35, 34 and computes based on the x-y pupil position 39 (determined from the High Speed Tracking System 21) a pupil offset correction information.

The coaxial mounting of the imaging device 32 with the optical axis of the diagnostic and/or treatment device provides accurate horizontal and vertical position measurement of the eye independent of depth changes. Furthermore, accurate torsional measurement is provided since the visual axis of the eye is normally aligned with the axis 37a. (may be supported by a fixation target), and therefore imaging of the eye is provided without geometrical distortions. In oblique eye positions geometric corrections can be applied using the known rotation and translation information of the eye.

The integration of imaging device 32 with the diagnosis and or treatment device can be made in either fixed (open loop) or eye stabilized (closed loop) embodiments.

Figure 4:
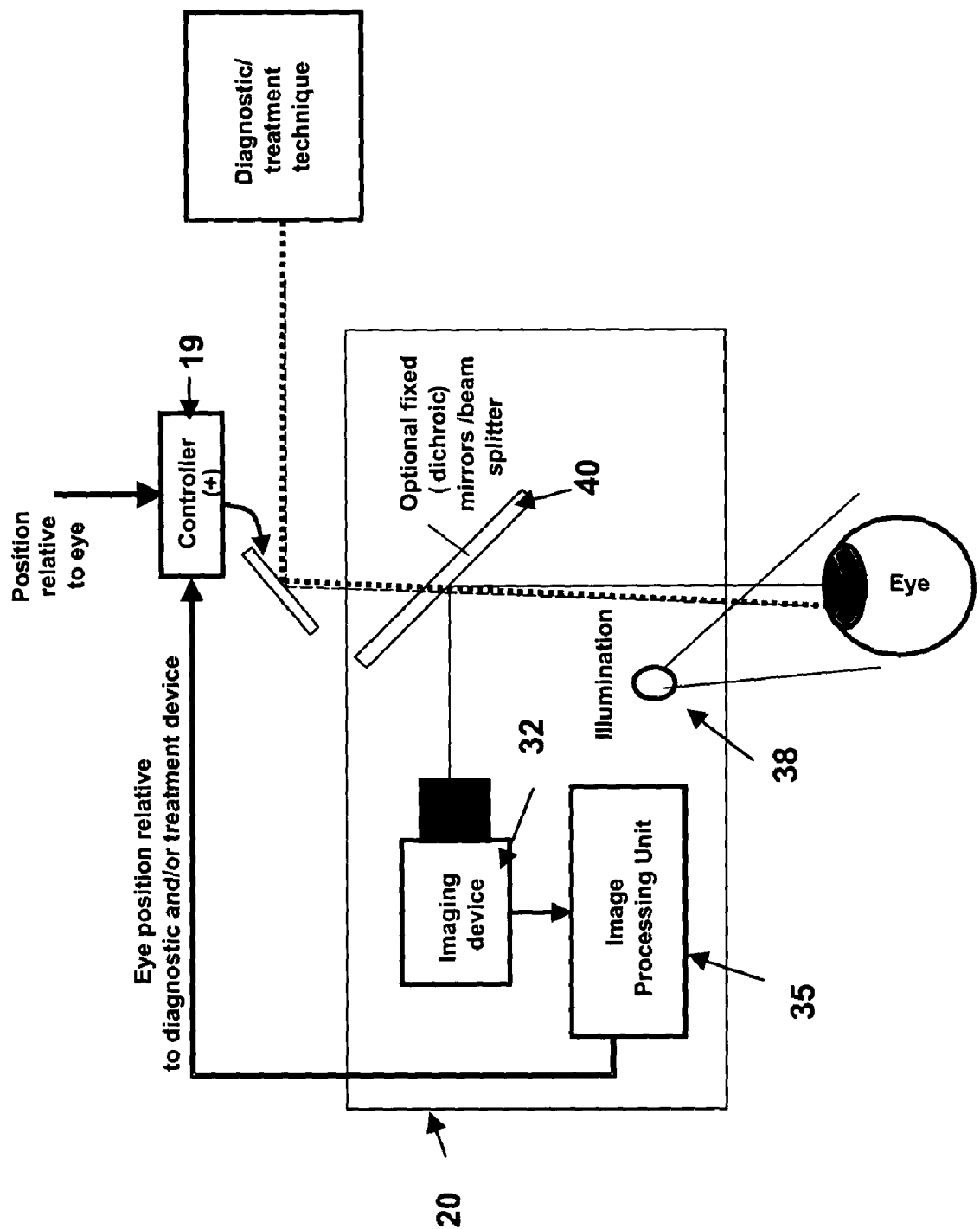
FIG. 4 shows the integration of the simplest version of the Eye Position Measurement System within the diagnostic and/ or treatment device.

In one possible embodiment described in FIG. 4, the imaging device 32 is viewing the scene directly—or if mechanically not possible—via a mirror or beam splitter 40. The scene is illuminated by the device fixed illumination system 38. The images obtained from imaging device 32 are then transferred to the image processing system 35. The eye position data, including compensated pupil position, torsion and rotation, are expressed in device-fixed coordinates, and then fed into the positioning control system 19 of the diagnostic and/or treatment device. This type of control usually requires synchronization between the ablation laser system and the eye tracker. If asynchronous communication is performed the overall latency may increase.

Figure 5:
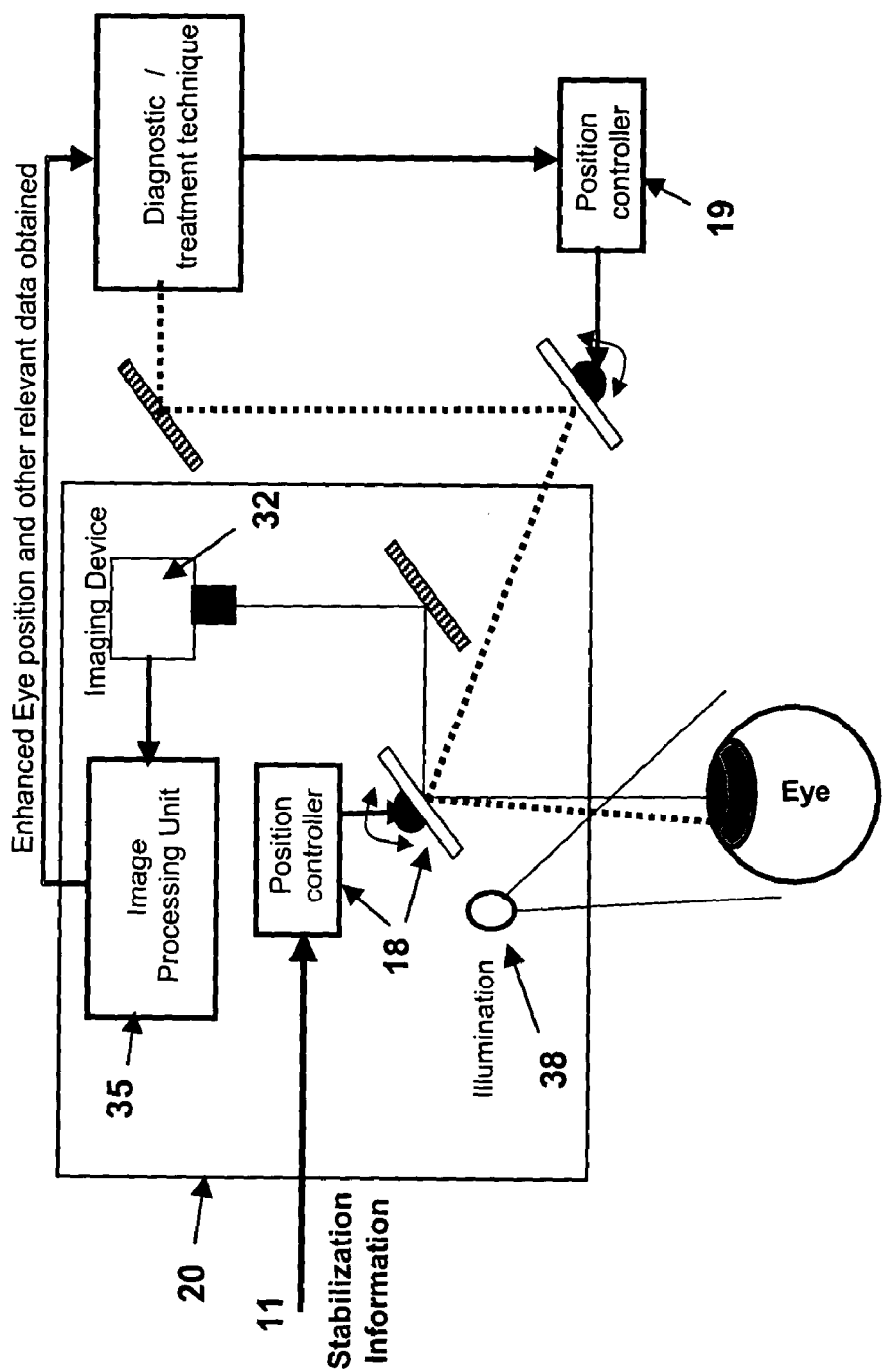
FIG. 5 is a block diagram showing stabilized image based tracking.

In another possible embodiment is described in FIG. 5: The imaging device 32 is viewing the scene via an x-y position controlled mirror system 18. The x-y position controlled mirror system 18 is controlled by the Stabilization information 11 forming a closed-loop tracking with the High Speed Tracking System 21. The closed-loop system insures that the image viewed by the imaging device 32 is always centered on the pupil by feeding an error position information to the x-y position controlled mirror system 18. In order to be effective, this information has to be provided from the high speed tracking System at considerably higher sampling rate than from system 20. An advantage of such a system is, that the diagnostic and/or treatment device is decoupled from the stabilization of fast horizontal and vertical eye movements, which has the effect of lowering the overall latency of the system. However, in order to correct for other types of eye position changes (such as torsion, pitch & yaw rotations, depth, or foreign object presence), the enhanced position information 12 provided by system 20 needs to be provided to diagnostic and/or treatment device.

1.2 Enhanced Imaging and Illumination

Figure 6:
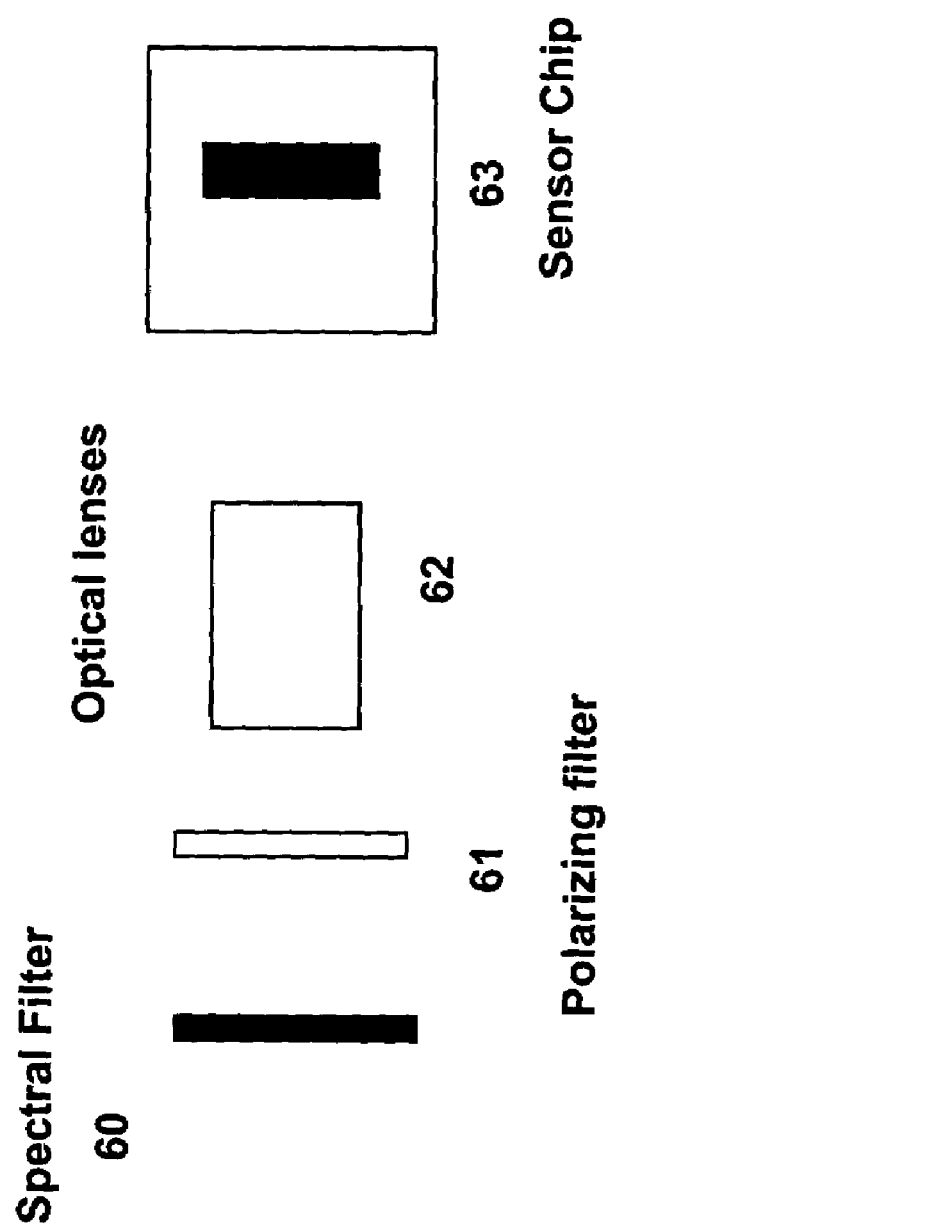
FIG. 6 shows the preferred embodiment of filtering for illumination.

Referring to FIG. 6, the imaging device 32, as well as all other additional imaging devices, can be either a color or a monochrome sensor chip 63 equipped with specific optical lenses 62, spectral filters 60 and/or polarization filters 61. The sensor chip 63 is sensitive to the specific spectrum of the light but not limited to IR in order to obtain specific features of the eye clearer. As example, if blood vessels on the sclera 73, or limbus border 71 shall be tracked, the invention uses green illumination and a monochrome sensor chip with a green color filter, or blue illumination and monochrome sensor chip with blue filter respectively. Alternatively, if illumination with white light is preferred, the blue or green color channel of a color sensor chip is used.

When several discrete aligned spectral responses have to be analyzed, e.g. different features from one imaging device, the invention uses monochrome sensor chip equipped with a multi-modal filter (e.g. IR & green) and structured illumination as a combination of modal wavelengths (e.g. IR & green).

Alternatively, the normal color filtering of commercial 3 chip RGB sensors is adapted to three other different selective wavelength areas. For example: 1 channel/sensor chip for IR to obtain a good contrast image of the pupil using IR light; 1 selective green or blue channel/sensor chip to obtain an image of blood vessels and/or the limbus using green/blue light; 1 channel/chip with a broad visible spectrum to obtain good image of the iris features using broad spectral light.

In a preferred embodiment, sensor chip 63 is a monochrome IR sensitive sensor and filter 60 is a bimodal passband filter (IR & green).

In addition to the light sources, which illuminate the eye from oblique angles, IR illumination sources can be optionally mounted normal to the eye to illuminate the eye directly from above and create a bright pupil effect ('red eye effect'). By alternated operation of this coaxial illumination between subsequent images and grey level difference estimation between subsequent images within the pupil area a more robust detection of the pupil is provided. In addition to standard imaging devices new CMOS sensors may be used to allow faster and more frequent selective readout of specific areas, lines or just pixels at specific areas.

The illumination 38 consists of one or several light sources at specific angles with selected wavelengths and polarization in order to provide maximum contrast of the specific features used.

Due to the optical characteristics of the cornea, the illumination creates specular and diffuse reflection components. Using polarized light and accordingly polarizing filters in front to the imaging devices, specular reflection (maintaining primarily the polarization) can be differentiated from diffuse reflection. As an example the imaging device 32 is equipped with a horizontal polarizing filter 61, while the illumination 38 is vertically polarized using a polarizing filter or other polarizing elements. This enhances the visibility of for example limbus and pupil due to attenuation of specular components.

With structured illumination a monochrome imaging device can be used to acquire a high contrast image with different landmarks. if the structured illumination illuminates each landmark with its optimum wavelength, i.e. an optimized structured illumination would illuminate the sclera with blue/green light to enhance visibility of blood vessels, near infrared illumination would be used for illumination of the pupil(-border) and more or less visible light would be used for illumination of the iris.

In a preferred embodiment, illumination 38 is a combination of IR and Green light produced using LED and/or laser diodes.

This setup also ensures that each feature can be illuminated with the appropriate intensity without increasing the total amount of light that falls into/onto the eye.

1.3 Image Processing

Figure 7:
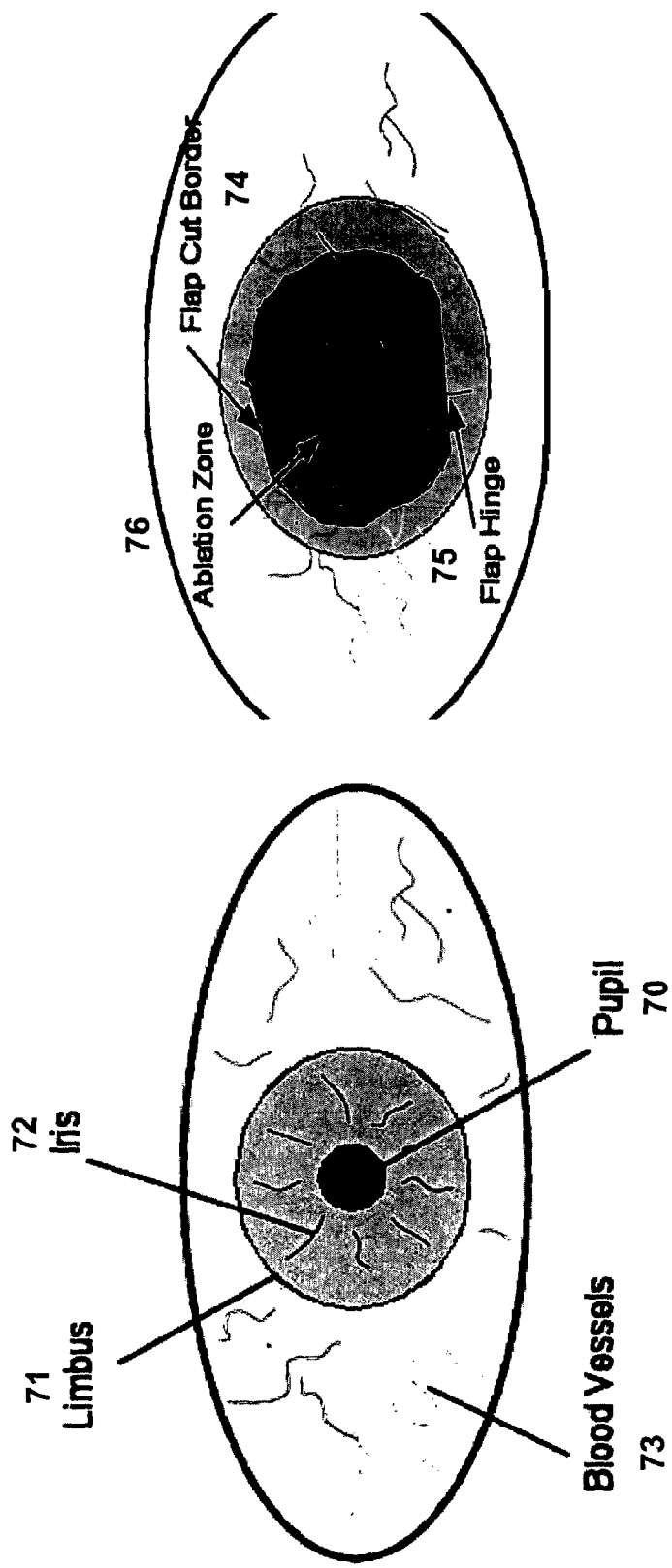
FIG. 7 shows possible features or landmarks of the eye that may be measured or tracked.

Image processing of the image obtained from imaging device 32 enables measurement of horizontal, vertical and torsional positions of the eye by determining the position of natural or artificial landmarks on the eye as shown in FIG. 7, such as among others pupil, iris structures, iris/limbus border, blood vessels, applied markers/marks, reflections of the illumination, LASIK flap borders of the cornea and also laser applied markings on the cornea.

1.3.1 Pupil Size Independent Tracking of the Eye

Pupil size independent tracking is obtained by periodically correcting any offsets of pupil center introduced by pupil dilation or other factors (optical distortions). The correction is realized by means of parallel tracking of reference points, which are known to be stable with respect to the cornea during surgery, such as for example limbus border 71. Due to fact that pupil size changes are rather slow (compared to horizontal and vertical eye movement), the required update rate can be significantly lower than the x/y tracking rate with the high speed tracking system.

Figure 8:
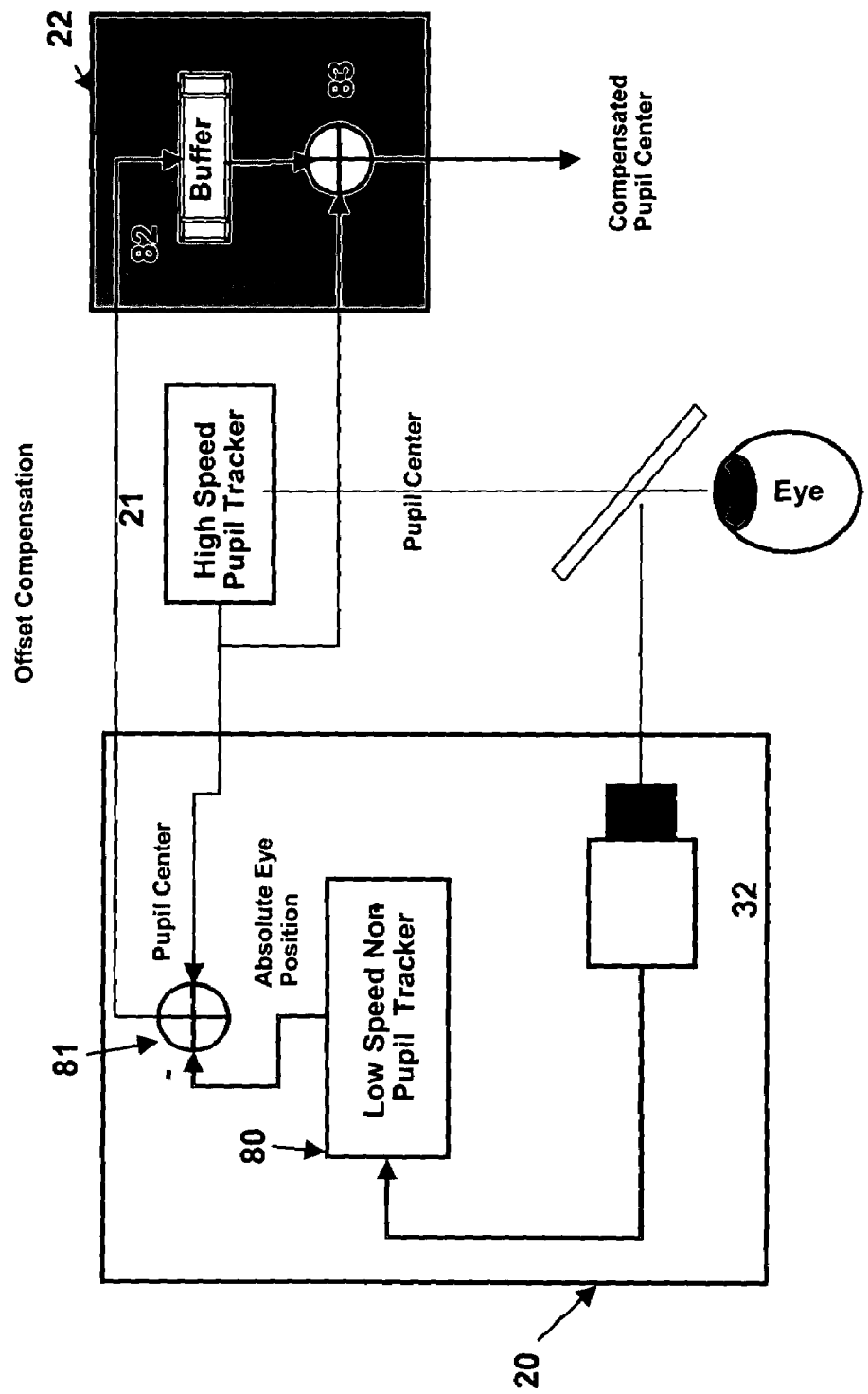
FIG. 8 illustrates the integration of the high speed pupil based tracking system with the eye position measurement system.

An integration of such system providing both fast and pupil size independent tracking is shown in FIG. 8. The image from imaging device 32 is fed into the non-pupil tracking system 80 that measures the non-pupil landmark position. The adder 81 computes the difference between the corneal-fixed feature and pupil center. The result, namely the offset compensation, is fed to the buffer 82. The corrected result is obtained by summing the current pupil position 83 with the offset compensation value stored in buffer 82. The update rate of the buffer is usually determined by the processing speed of the Eye Position Measurement system and normally slower than the sampling rate of the High-Speed Pupil Tracker 21.

The parts 80 and 81 are modules of the image processing system 35. The parts 82 and 83 are belonging to system 22.

The algorithm for non-pupil tracking consists of two phases: initialization and tracking.

Figure 9:
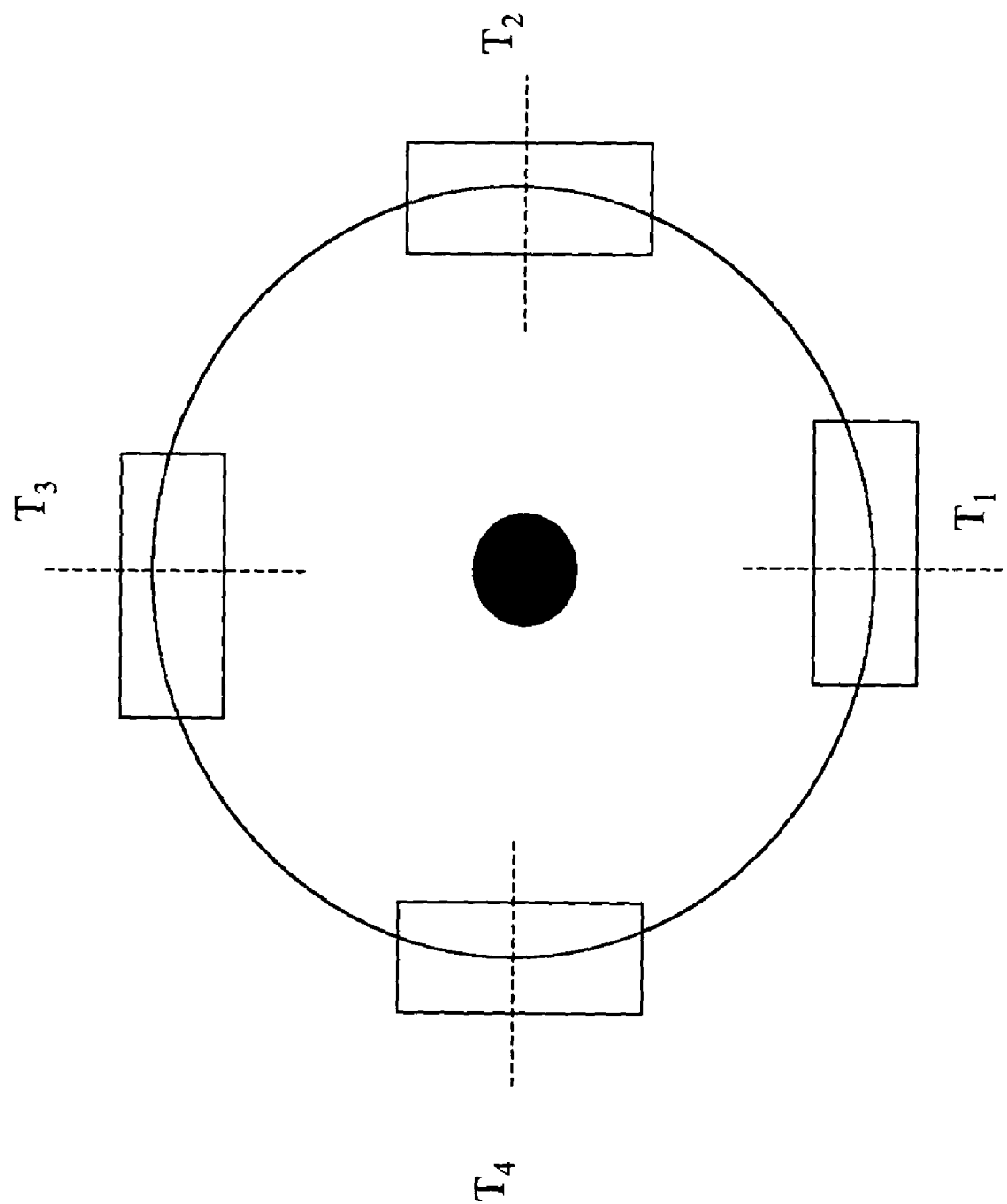
FIG. 9 shows the image templates relative to the pupil center for limbus tracking.

In the initialization phase, an eye image snap shot is taken as the "reference frame", defining reference point (the pupil center of this image) and time to which further pupil center shifts will be reported thereafter. The reference image is then analyzed in order to determine meaningful and detectable features present in the image. Meaningful refers to the property of the feature to be immobile with respect to the cornea. This is done by a priori knowledge of the eye model incorporated in the image processing algorithm (for example it is known that limbus is a meaningful feature and therefore model of limbus, including expected limbus diameter is incorporated for easy recognition). Detectable refers to the property of the feature to be visible and feasible to be tracked by image processing means. The detection is done by search of regions with high gradient in both horizontal and vertical directions, or combinations of areas or templates with high gradient in either the horizontal or vertical directions. Usually this corresponds to limbus border together with blood vessels. A number of such regions are stored as image templates T1, T2, T3, T4 together with their position relative to pupil center. An example for the location of such templates is shown in FIG. 9. Knowledge of the iris diameter and maximum expected pupil center shift can be used to set a Region of Interest from the pupil center, as determined either by a separate pupil-based tracking algorithm on the same image or by the High Speed Pupil based tracking Sub-System 21.

In the tracking phase, each previously stored region is localized in the incoming new image by means of two dimensional cross-correlation techniques. The similarity measure for correlation used in the preferred embodiment is normalized cross correlation (NCC) for its properties of invariance to moderate changes in global illumination and robustness to noise. Other techniques, like sum of squared difference or sum of absolute differences, can be also used. Sub-pixel resolution is obtained through interpolation of correlation values The position of each template relative to current pupil center can be weighted using the confidence level of the template match to calculate the pupil center shift.

1.3.2 Torsional Eye Tracking

Figure 10:
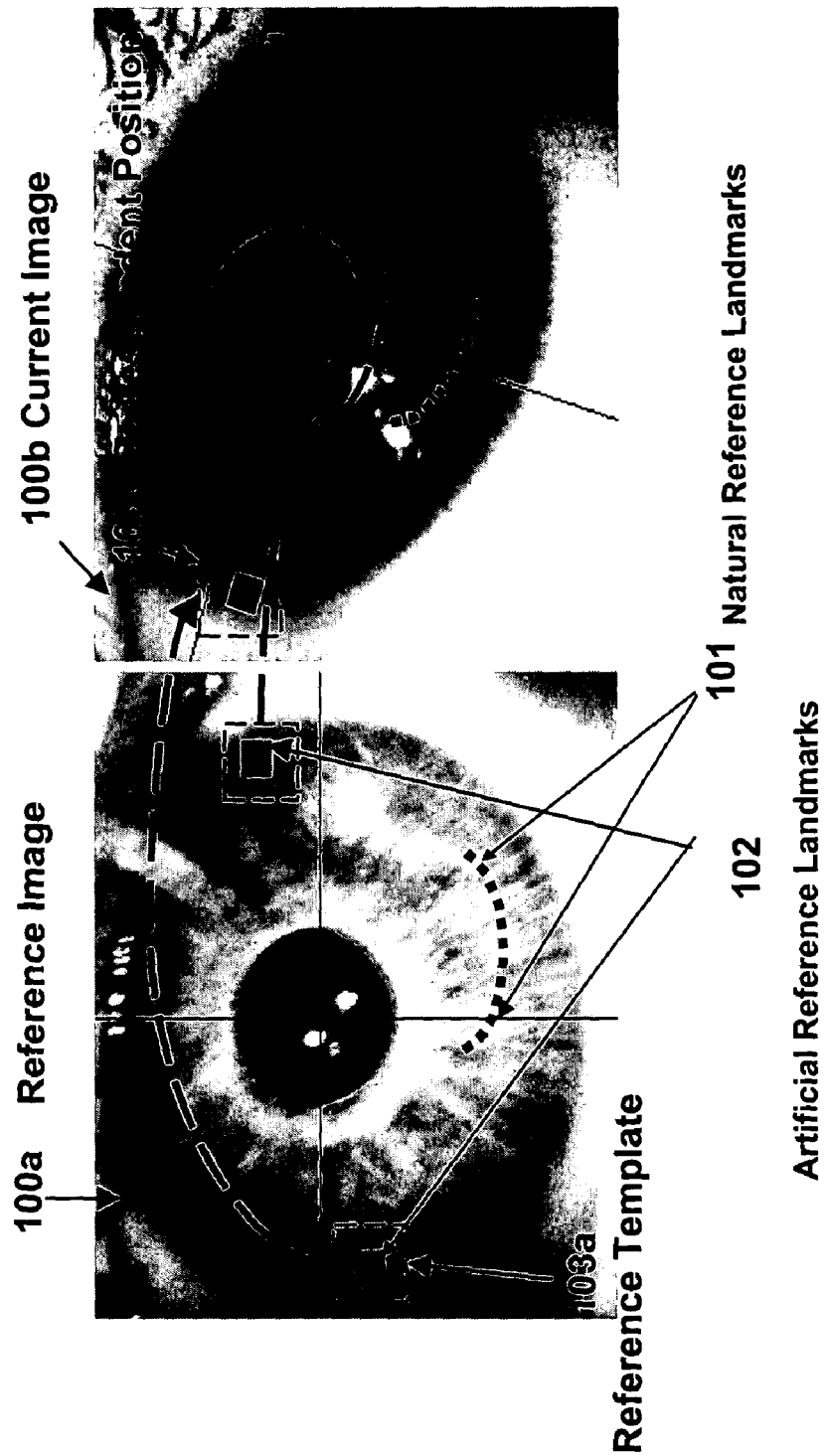
FIG. 10 illustrates torsion measurement with automatically detected reference points.

FIG. 10 shows the eye torsion measurement by means of registration of at least two distinct landmarks on the eye as shown in FIG. 7. The algorithm consists in two steps: initialization and tracking In the initialization step, a reference image 100a is acquired and analyzed in order to determine the suitable landmarks for registration 101, 102. The selection criteria of tracking registration points is based on the local intensity of the gradient along radial direction together with possible a priori knowledge about their approximate position, color or shape (like in the case of artificial markers 102).

A number of such reference points are stored as image templates together with their position relative to pupil center.

In the tracking step, the template of each reference point 103a, is searched in the incoming image by means of cross-correlation techniques, depicted as dotted line in FIG. 10. Once the correspondent position 103b is obtained for each reference point, the torsion between the reference and current image is computed by optimal least-squared approximation of rotation matrix of the reference template and correspondent template.

In a preferred embodiment, the scleral blood vessels are used as landmarks. The visibility of blood vessels is insured by the use of enhanced structured illumination with IR-Green wavelength combination. The location of blood vessels is based first on knowledge about pupil position and iris dimensions. This limits the search area to the outside parts of limbus border.

Further on, the selection of vessels is based on the local contrast and directionality properties of the image.

1.3.3 Eye Rotation from Combination of Head Tracker and Eye Tracker

Figure 11:
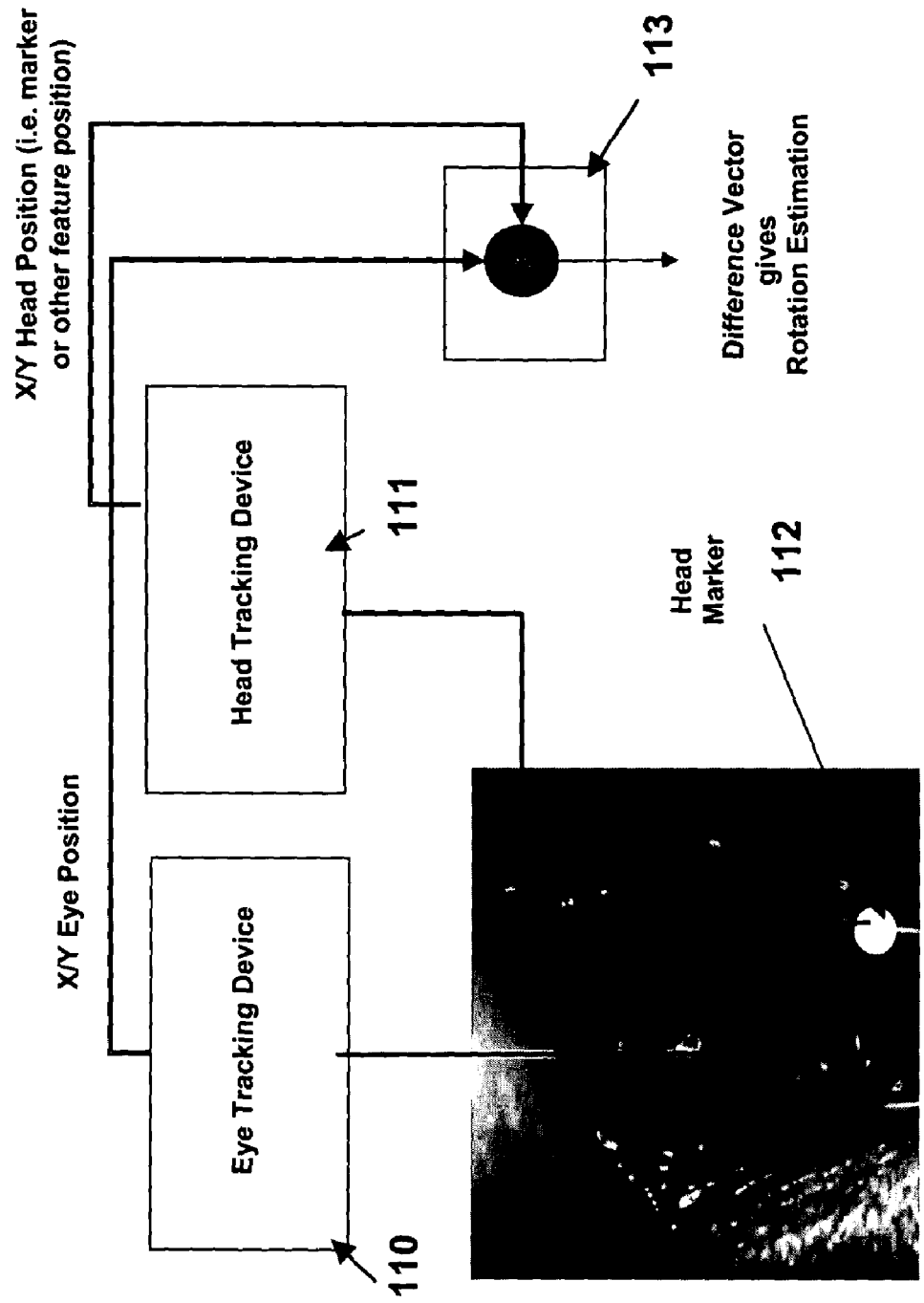
FIG. 11 is a block diagram showing the combination of eye tracking and head tracking for rotation measurements.

The method and apparatus of measuring eye rotation is depicted in FIG. 11. The head x/y position, computed by subsystem 111 is subtracted from the eye x/y position delivered by subsystem 110 (i.e. using the limbus tracking module described before).

The head tracking functionality is realized by placing a small marker 232 fixed to the head in a place visually accessible by a imaging device. Candidate locations are: eye-lid clamps, eye corners or the forehead of the patient. A specific image processing module tracks the marker in the obtained image. Instead of markers specific characteristics of clamps may be directly used for tracking.

The amount of eye rotation is proportional with the variation of difference between head position and eye position, $R_x = x_H - x_E$, $R_y = y_H - y_E$.

Figure 12:
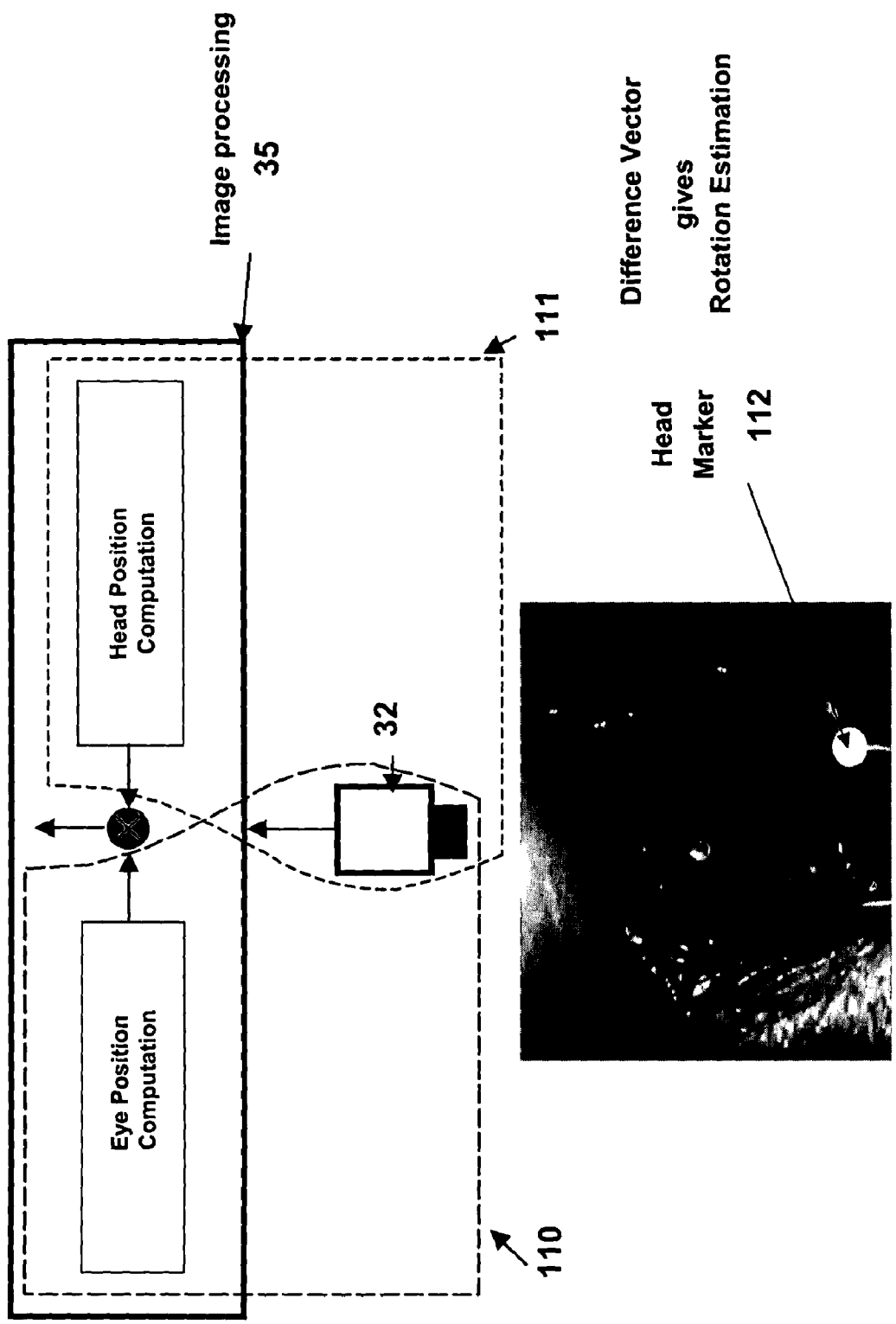
FIG. 12 is a block diagram showing the combination of eye tracking and head tracking for rotation measurements, when the same physical system is used for imaging the head and eye.

In one possible embodiment shown in FIG. 12, the marker 112 is placed on the eye-lid clamp, the head tracking system 111, and eye tracking 110 are accomplished with same imaging device, 32, and image processing system 35.

Alternatively, the two functional blocks can be implemented with distinct imaging devices if, for example, the position of head marker 112 does not allow to be imaged together with the eye.

1.3.4 Foreign Object Detection

Figure 13:
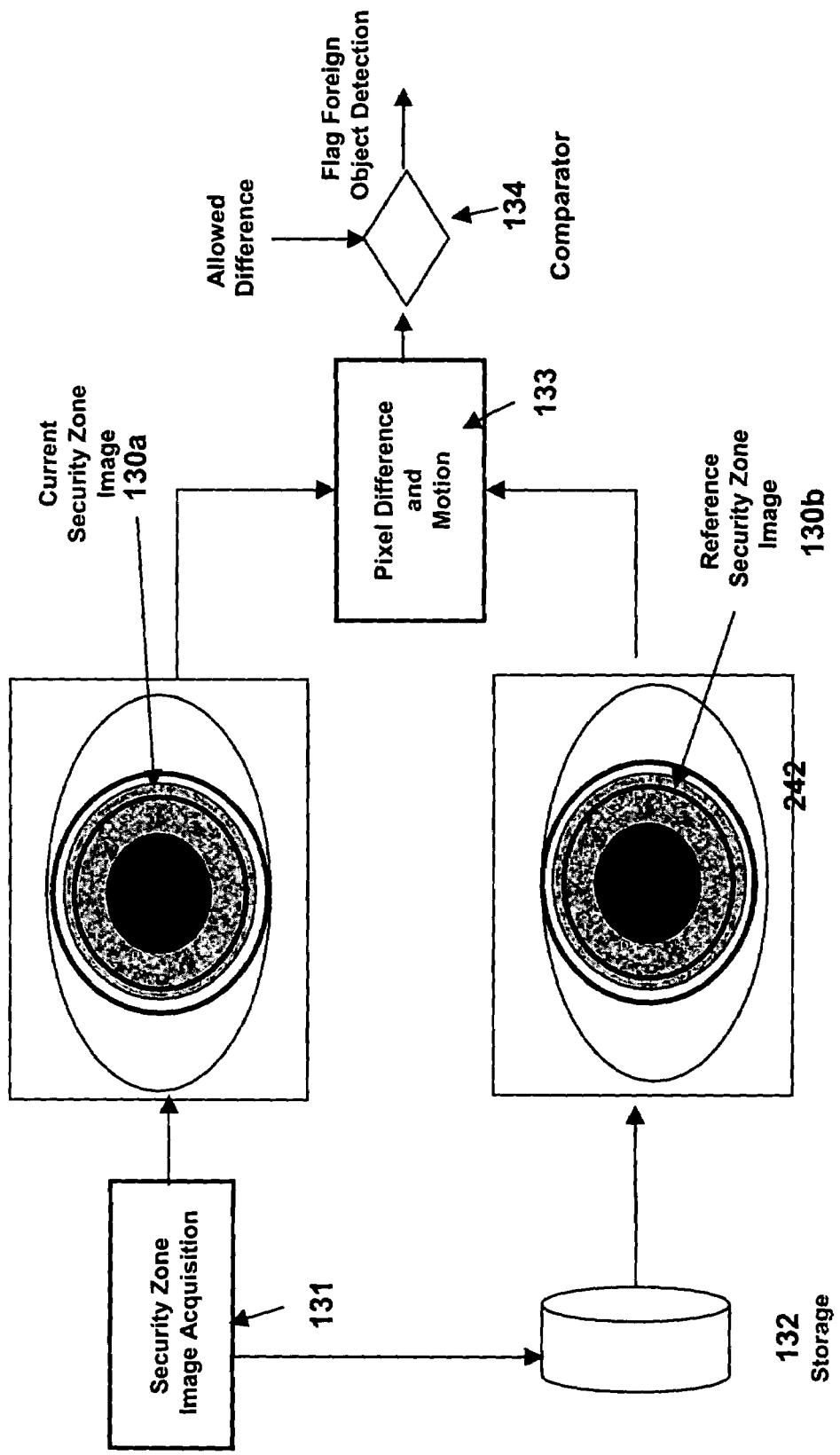
FIG. 13 is a block diagram of foreign object detection with 1 camera based on motion and appearance.

Presence of foreign objects in the ablation area is flagged by system described in FIG. 13. The system 131 is able to detach and normalize a specific region from an eye—so called "Security Zone" normally located outside and around the diagnostic or treatment zone, and usually corresponding with the limbus boarder location in the image. The system 131 is used first to store a reference image of the security area 130b, in the storage device 132 and t. The time of acquiring the reference image may be triggered by the operator or automatically determined during the procedure. After the "Reference Security Zone" a similar security zone may be extracted from the following images, centered around the detected eye position (Current Security Zone Image 130a). The images 130a and 130b are then compared by system 133. If the difference exceeds a maximal admitted value, the comparator 134 flags the presence of foreign objects.

Referring to image 14, the system 131 consists of one imaging sensor, for example imaging device 32, and the image processing system, 35. The image processing system analyses first the eye position in terms of translation and torsion with system 140. Then, image is aligned/normalized by performing a digital translation and rotation, 141. The aligned/normalized image is then cropped 142 in order to produce the security zone image.

The image comparison 133 can simply consist in performing a digital difference of the two images. Alternatively, if the analysis is extended on multiple frames, more complex methods, like coherency of optical flow, can be used.

1.4 Additional Off-axis Imaging Devices

Figure 15:
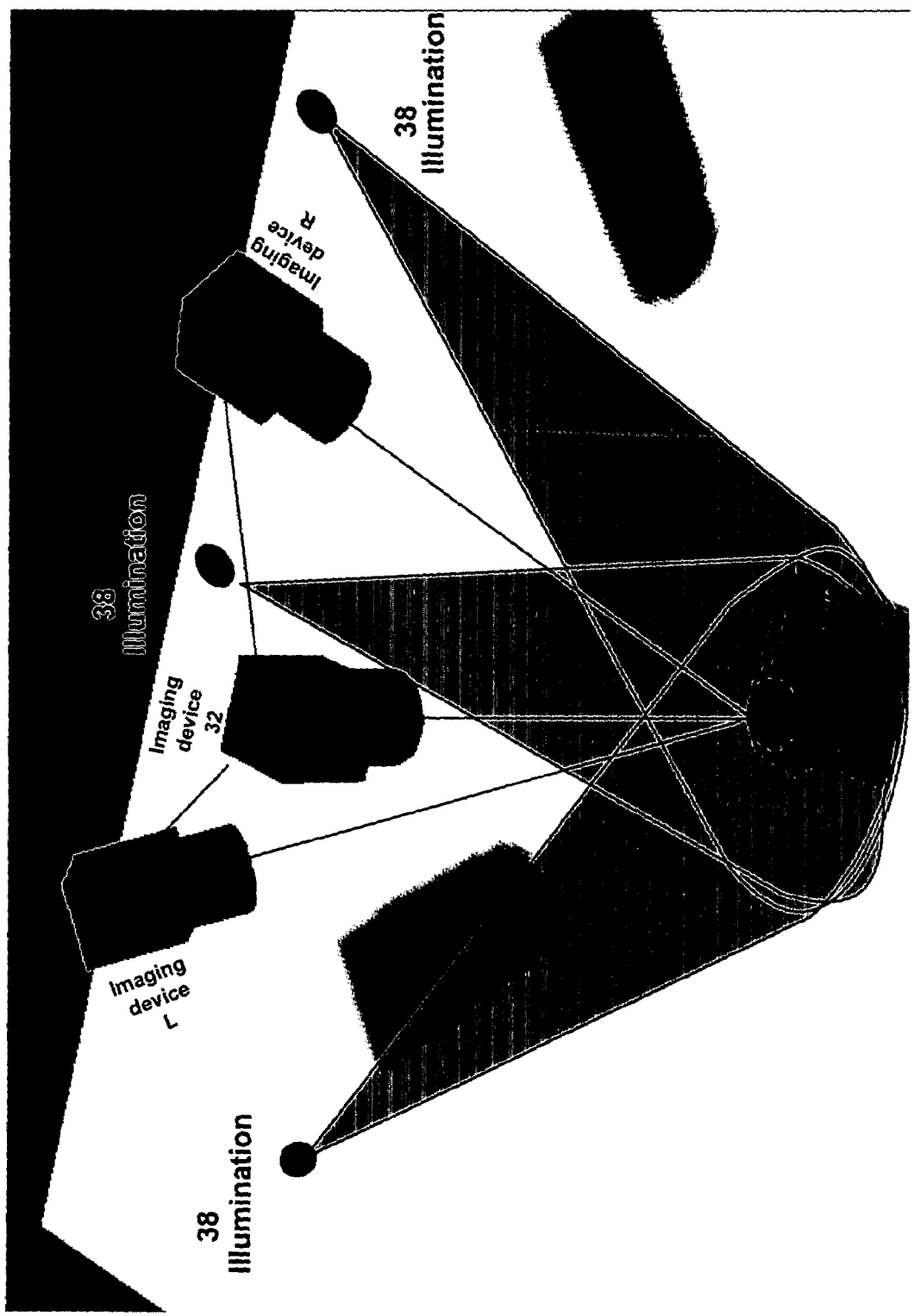
FIG. 15 shows the multiple camera system, with one direct viewing on-axis camera.
Figure 16:
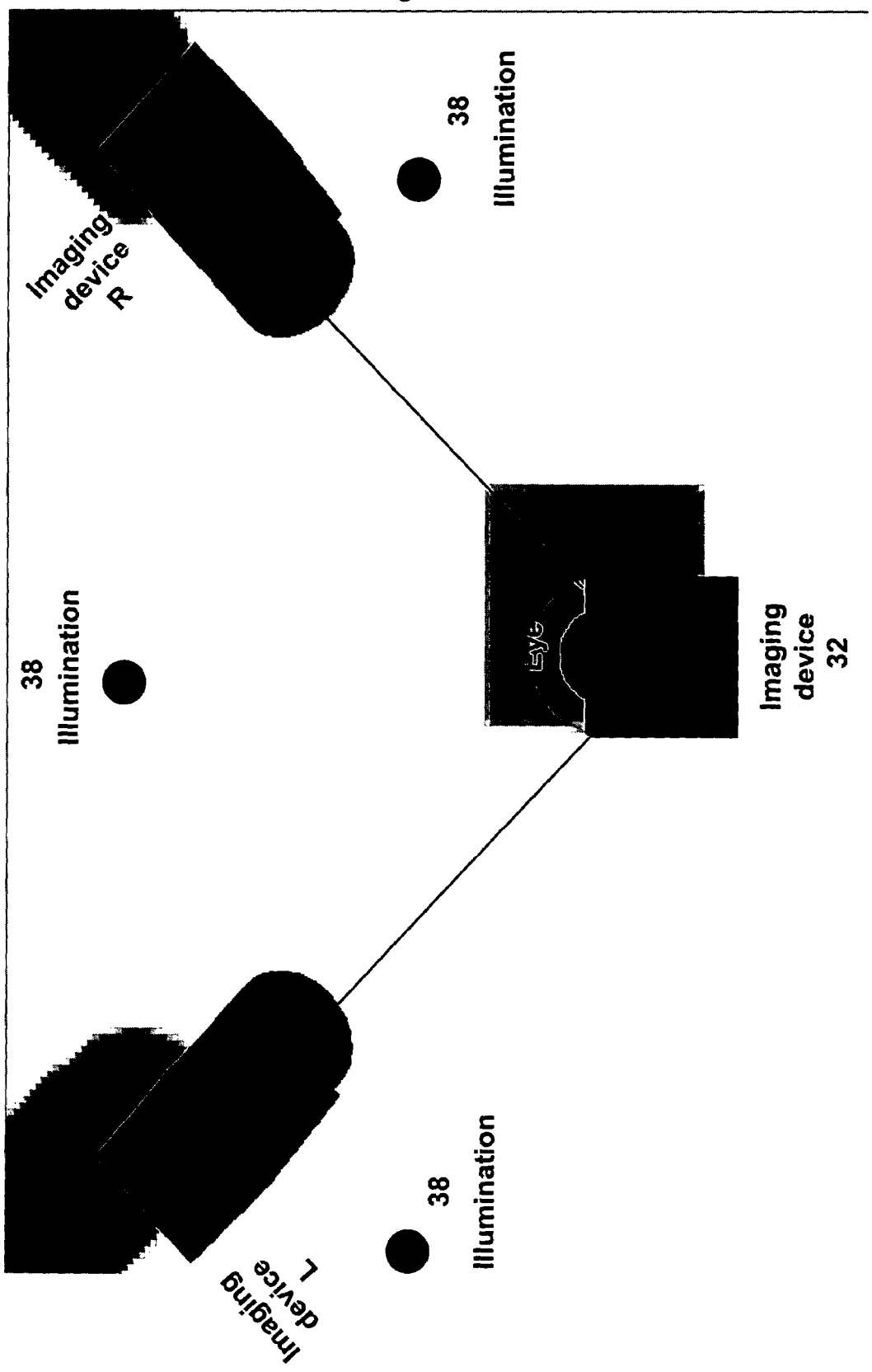
FIG. 16 is the top view of the same system shown in FIG. 16.

Referring to FIG. 3, the preferred embodiment of the subsystem 33 together with subsystem 32 is shown in FIG. 15 and FIG. 16. Here, two additional imaging devices L and R are viewing the eye from an oblique position, having their optical path tilted against the optical axis of the imaging device 32 which is coaxial with the diagnostic and/or treatment device.

The purpose of using at least one off-axis mounted imaging device in addition to the coaxially mounted imaging device is to provide an enhanced depth measurement. If multiple off-axis imaging devices are used, they have to be positioned in such a way that the eye does not lie on the same plane. Furthermore, the optical path of at least two imaging devices has to be distinct in order to allow use of binocular or trinocular stereopsis methods. In the preferred embodiment all optical paths are distinct.

Images from Imaging device L and R are transferred to the image processing system 35. All three imaging devices may be synchronized in order to allow image acquisition at the same time or at a precise time delay between imaging devices 32, L, R.

Figure 17:
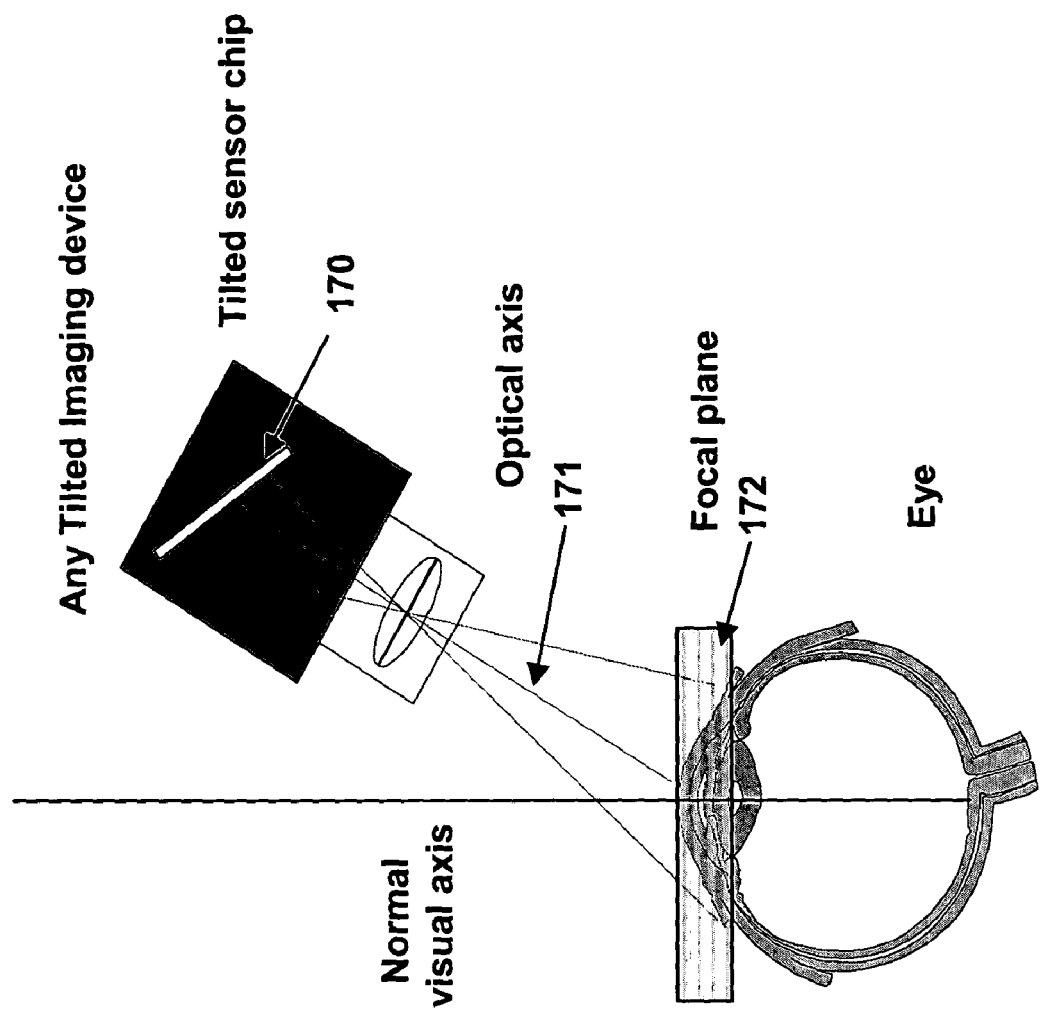
FIG. 17 shows a technique for compensating limited focal depth and geometric distortion of the off-axis imaging device by tilting imaging sensor chip to the optical axis.

As shown in FIG. 17, best results for the tilted imaging devices (i.e. Imaging device R and L) are achieved, if the light sensing sensor 170 of the imaging device (i.e. CCD- or CMOS sensor) are tilted against the optical axis 171 of the used lens. This sensor tilt is adjusted in such a way that the focal depth 172 of the corresponding imaging device in the plane of the iris or cornea (plane perpendicular to visual axis of the eye in the normal position) is constant, resulting in equally focused acquired image of the eye. Furthermore this positioning allows a better transformation of position data obtained for landmarks in the three sensor coordinate systems.

1.4.1 Depth Measurement

Distance of various eye-points along the optical path of the diagnosis and/or treatment device 37a (referred here as depth) can be measured whenever at least two optical axes of sensors 32 and 33 are distinct.

Figure 18:
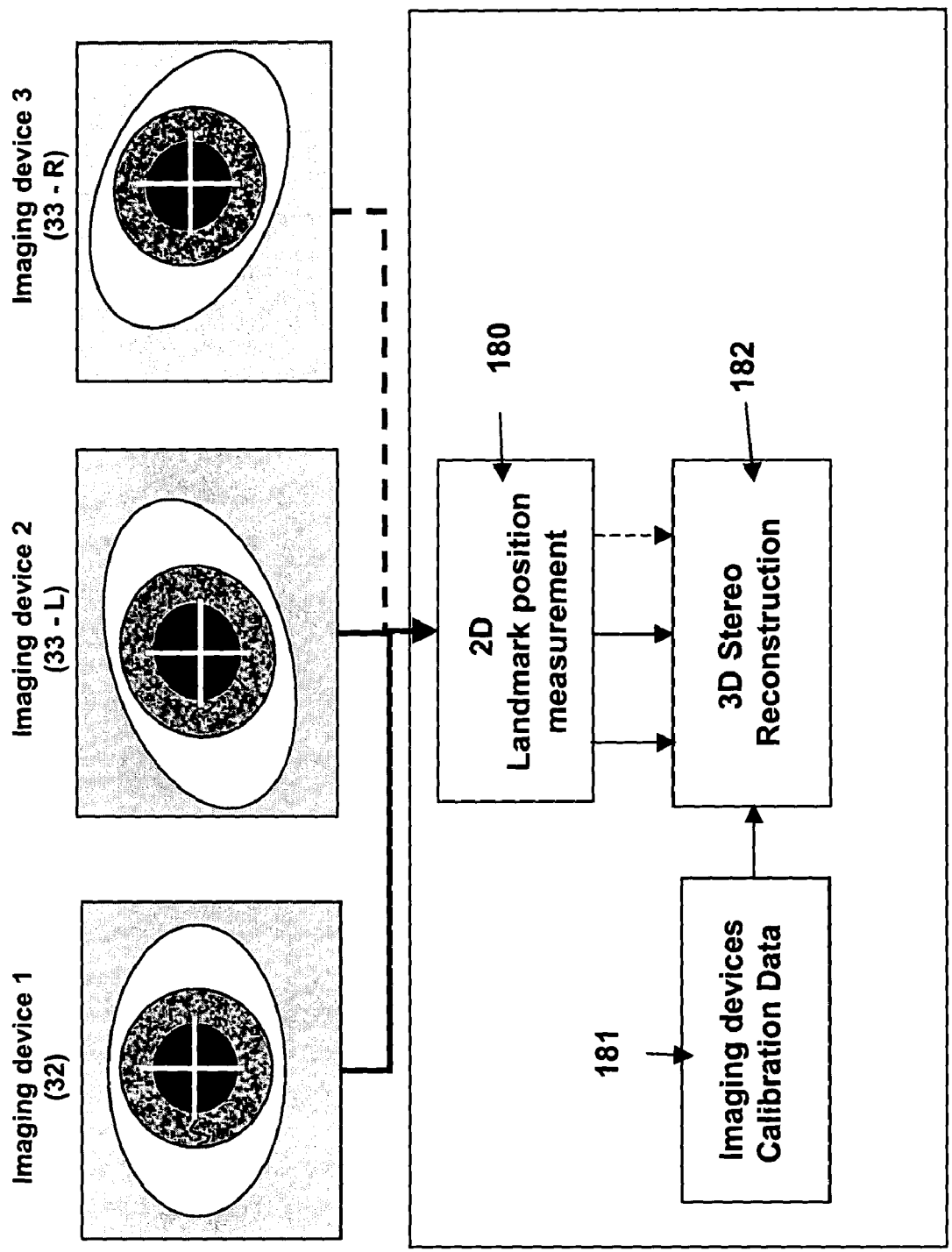
FIG. 18 is a block diagram of the information flow required for three dimensional stereo reconstruction from multiple cameras.

In the preferred embodiment, as shown in FIG. 15 and FIG. 16, all three optical axes are distinct from each other. The method of obtaining depth is illustrated in FIG. 18. Two images from different angles are acquired synchronously from the imaging devices 32 and imaging device 33 (R). Optionally additional images from imaging device 33 (L) may be acquired at the same time. Although not required, an increased number of sensors allows more robust and more accurate measurements. The absolute 2 dimensional position of a certain landmark of the eye (here for example shown for the pupil) is computed for each of the acquired images by module 180 in the pixel coordinate system of each imaging device. The imaging device calibration information 181 contains data describing the geometry and characteristics of the imaging device system, such as distance and orientation between imaging devices, focal length, etc. The set of 2D pixel positions delivered by 180, along with the imaging device calibration information 181, is fed into the stereo reconstruction module 182. Based on well-known formulas of 3 dimensional reconstruction, the position of the specific landmark in real world coordinates (mm) is obtained from each pair of images. If more than two imaging devices are used, redundant information is obtained. This redundant information is used to obtain increased robustness and accuracy by filtering the data such as averaging for increased precision, or median filtering for elimination of seriously corrupted data.

Depth measurement can be performed in multiple eye points using the above mentioned method and system and other landmarks such as iris features, limbus, scleral blood vessels and artificial markers.

Figure 19:
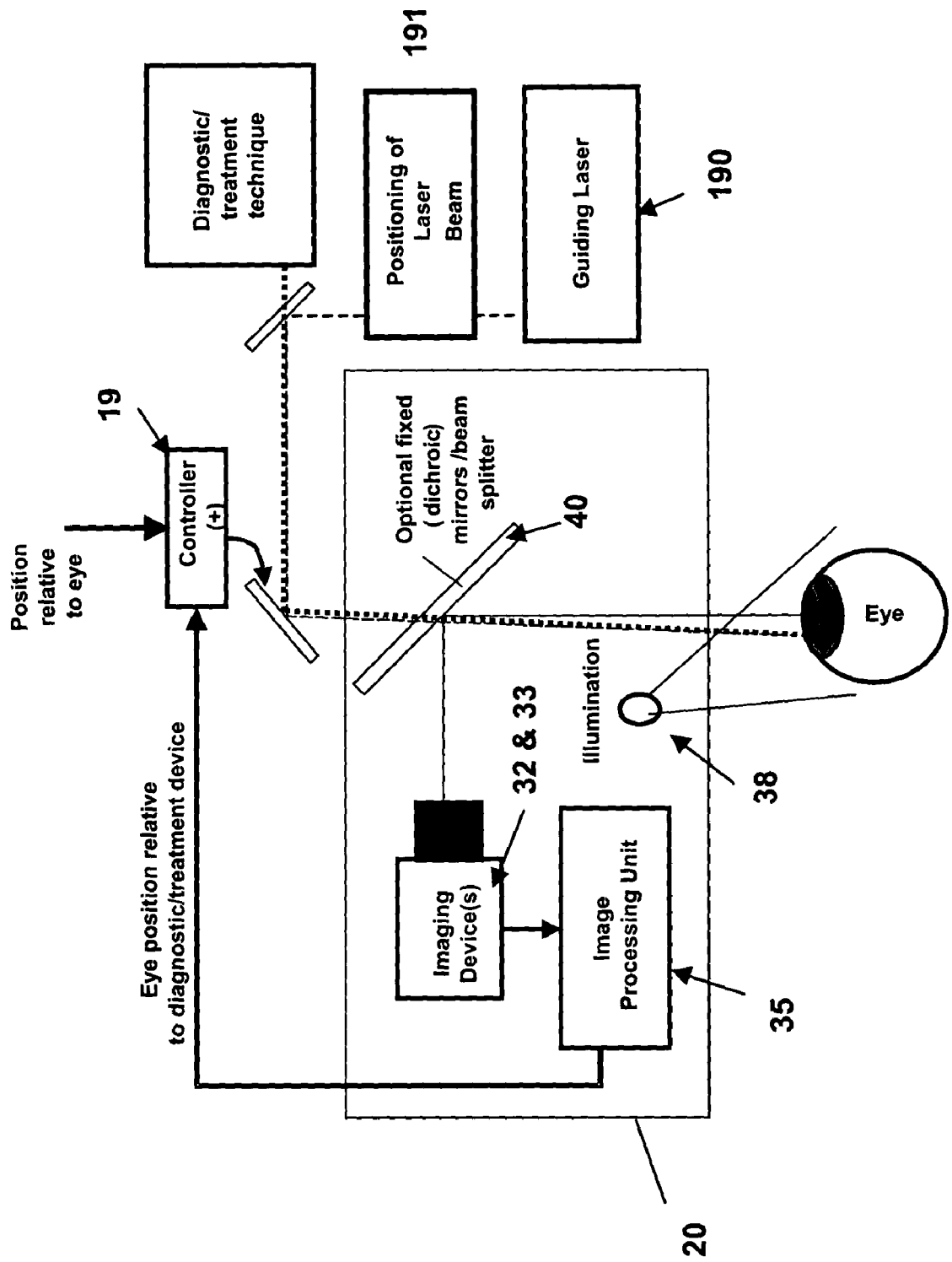
FIG. 19 is a block diagram of the system for tracking a guided laser reflection in order to measure treatment or diagnosis position.

Measurements of depth to the corneal surface can be obtained also using an additional guidance laser beam pointing on the desired point on the cornea as shown in FIG. 19. The guidance laser beam 190 may be optionally oriented relative to the diagnostic/treatment axis using an additional x/y positioning system 191. The diffuse part of the reflected light from the corneal surface is imaged by imaging devices 32 and 33 using according polarization filters. Image processing on order to determine the location of the reflection on the cornea in multiple camera images and subsequent 3D reconstruction provides a 3D position of the cornea at the reflection on the cornea. If the guidance laser is coaxially aligned to the ablation laser beam, a continuous measurement of a 3D position of the treatment point on the cornea can be obtained. It also allows automated and objective calibration and verification of the calibration between the two coordinate systems of the tracking system and diagnosis/treatment system.

Alternatively, the guidance laser can be moved with respect to the ablation one, by either a fix or variable displacement.

The height information (z) can be used for adjusting the energy and focus of subsequent laser shots. Alternatively, height can be measured just before the ablation laser shot with the guidance laser.

Furthermore, using the 3D position information on multiple specific points on the eye, additional measurements, like eye rotation and/or foreign object detection, can be performed.

1.4.2 Eye Rotation Measurement

Figure 20:
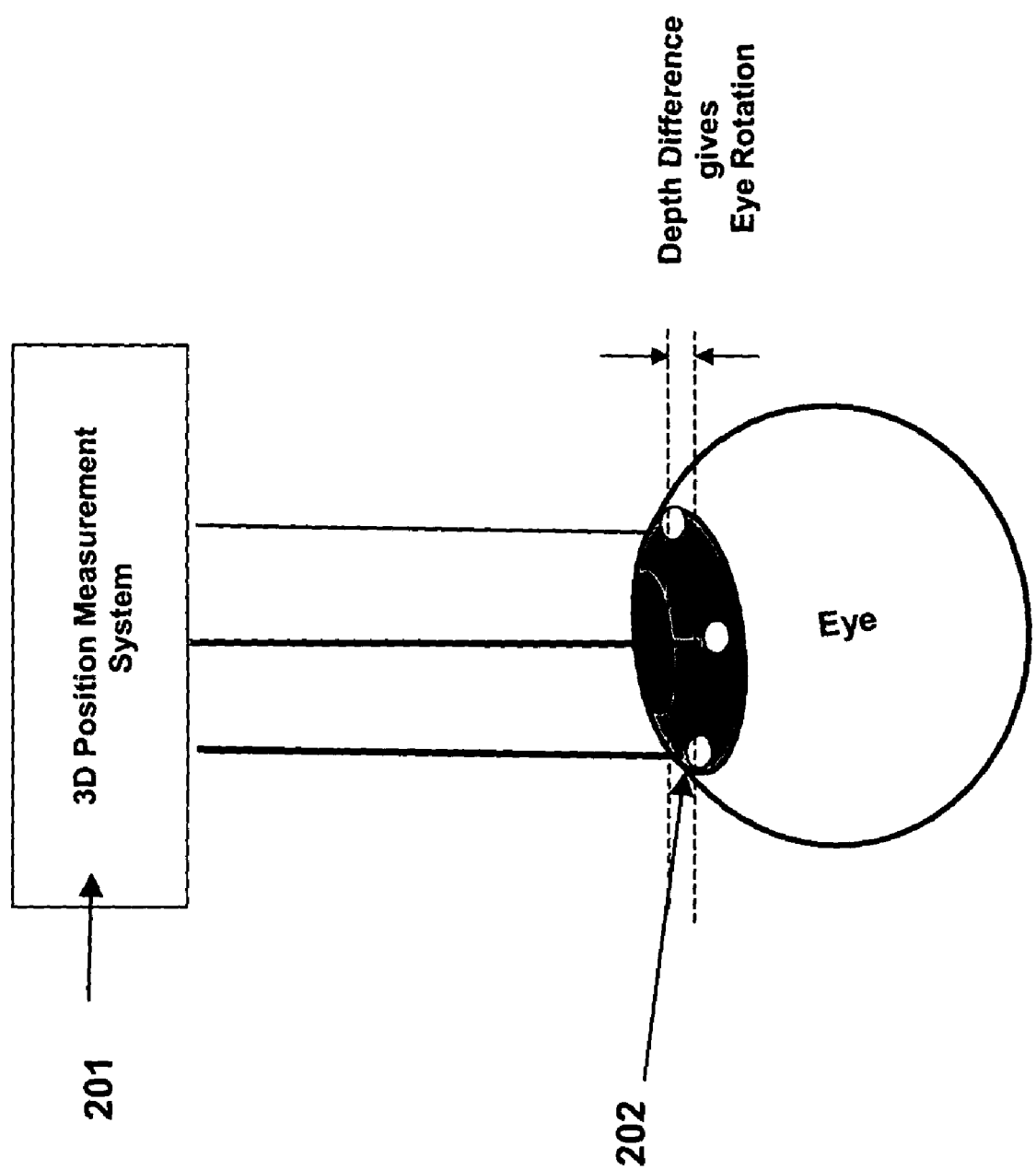
FIG. 20 illustrates the method of finding eye rotation from depth measurement at multiple points.

The method and apparatus for eye rotation measurements is presented in FIG. 20. It consists of a set of eye fixed landmarks 202, and a 3D position measurement system 201 that is capable of delivering 3D positions of each of these landmarks. The number of landmarks should be at least 3 for allowing the determination of all three rotation angles (pitch, yaw and roll) of the eye. Any of the previously mentioned landmarks may be used by this method. The method consists of three steps:

1. Acquire the 3D reference position of a set of landmarks on the eye in a defined reference position or time (for example at the beginning of a treatment or diagnosis) or at a reference position (for example when optical axes of the eye is aligned with the optical path of the treatment/diagnosis device)

2. Acquire the 3D position of the same set of landmark at each of the following "current" images.

3. Compute the change of orientation between the reference and current set of 3D positions using three-dimensional registration, for which well-known algorithmic solution exists.

The method above described results in the 3 angular rotations around x, y, and z axes.

In a preferred embodiment the 3D positioning system and method is the one in FIG. 18. The landmarks are chosen to lie in the same plane. The plane is chosen to be perpendicular to the optical path of treatment/diagnosis device when eye is in "null" rotation position. For example the landmarks can be various structures of iris or parts of limbus border. In this way the orientation problem is simplified since it resumes to finding the orientation of the plane which best approximates the 3D positions of set of landmark.

Figure 21:
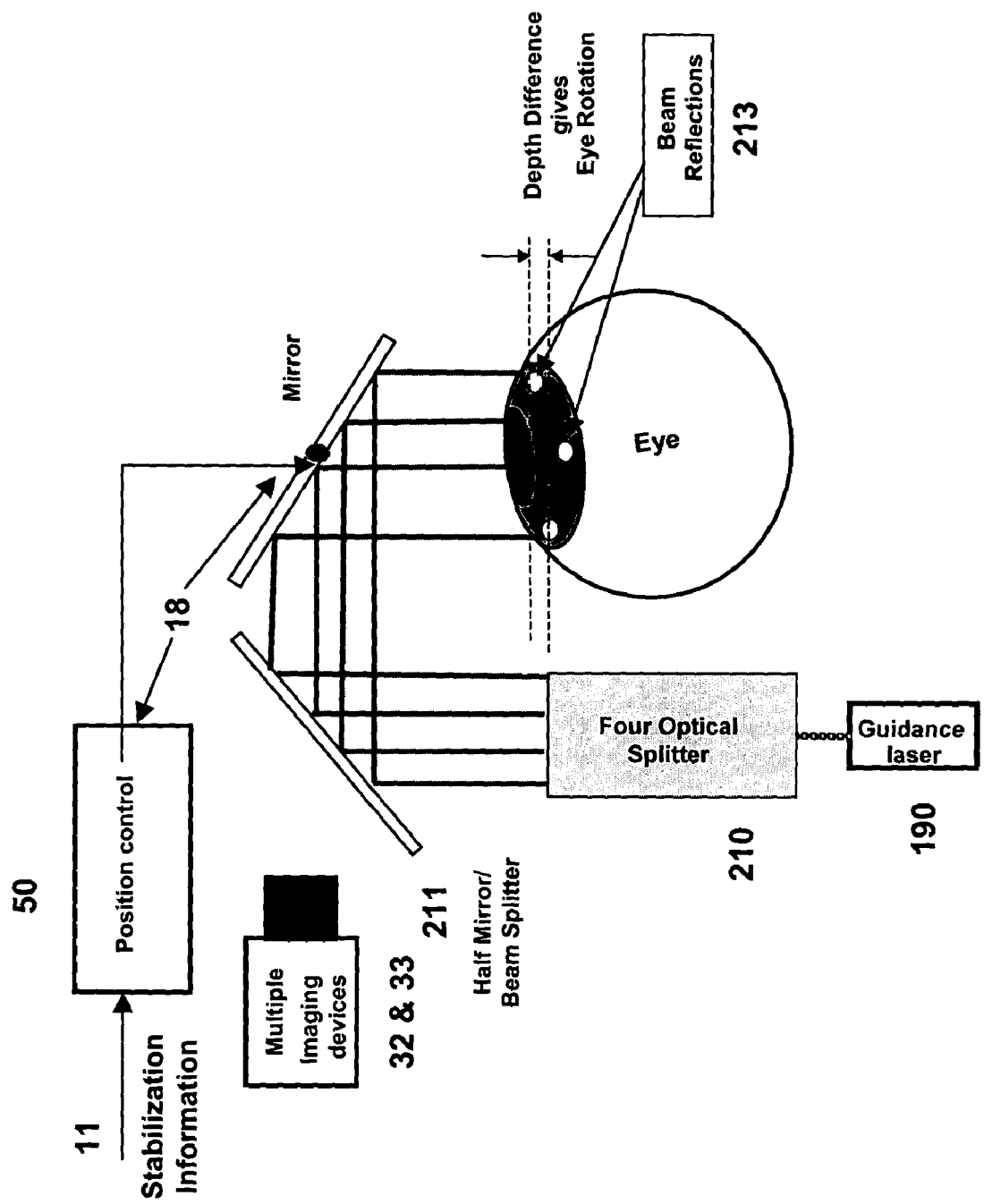
FIG. 21 shows how multiple reflected light sources can be used as reference points in the technique described in FIG. 20.

Optionally, the landmarks can be virtually created by imaging the diffuse reflection of multiple guidance laser beams. The system is described in FIG. 21. The guidance laser 1901 uses a wavelength visible by sensors 32 & 33, (e.g. near IR). The laser beam is split into four or more spatially displaced beams by the optical splitter 210. The four outputs of the optical splitter are directed to the eye via the x/y position controlled mirror 18. This provides an eye stabilized optical path for the laser beams. This means that the reflections of the laser beams 227 (referred as virtual landmarks) are always formed in the same horizontal and vertical position with respect to the eye, which now can be used by the above described rotation measurement apparatus and method.

Foreign object detection can also be accomplished using a general depth measurement system as shown in FIG. 22. The method consists of measuring the depth with system 220 (distance along system's optical axis) using a large number of test points, 224, distributed over the surface of the eye. The distribution of test points can be either regular (e.g. rectangular mesh), random, or following a certain boarder (e.g. along pupil or limbus border). Since eye position variations along optical axis are small, any foreign object can be detected, if a certain number of test points are detected to closer to the treatment/diagnosis device (Foreign Object Zone 221) than a defined Threshold depth 222. Objects inside the Eye Zone 223 are considered belonging to the eye. In order to clearly distinguish between the eye and foreign objects, the volume of the eye zone shall be minimized. This can also be accomplished by the use of non-planar borders, for example a curved surface parallel to the cornea.

In a preferred embodiment, the depth measurements are performed using the method and apparatus described already in FIG. 18. The number of points in which the depth measurement is performed is fixed as a rectangular grid of 3×3 points as shown in FIG. 22b.

Alternatively, the depth measurements can be performed using specialized depth measurement devices like range sensors or OCT.

1.5 Additional Non-Image Based Sensors for Depth Measurement

Figure 23:
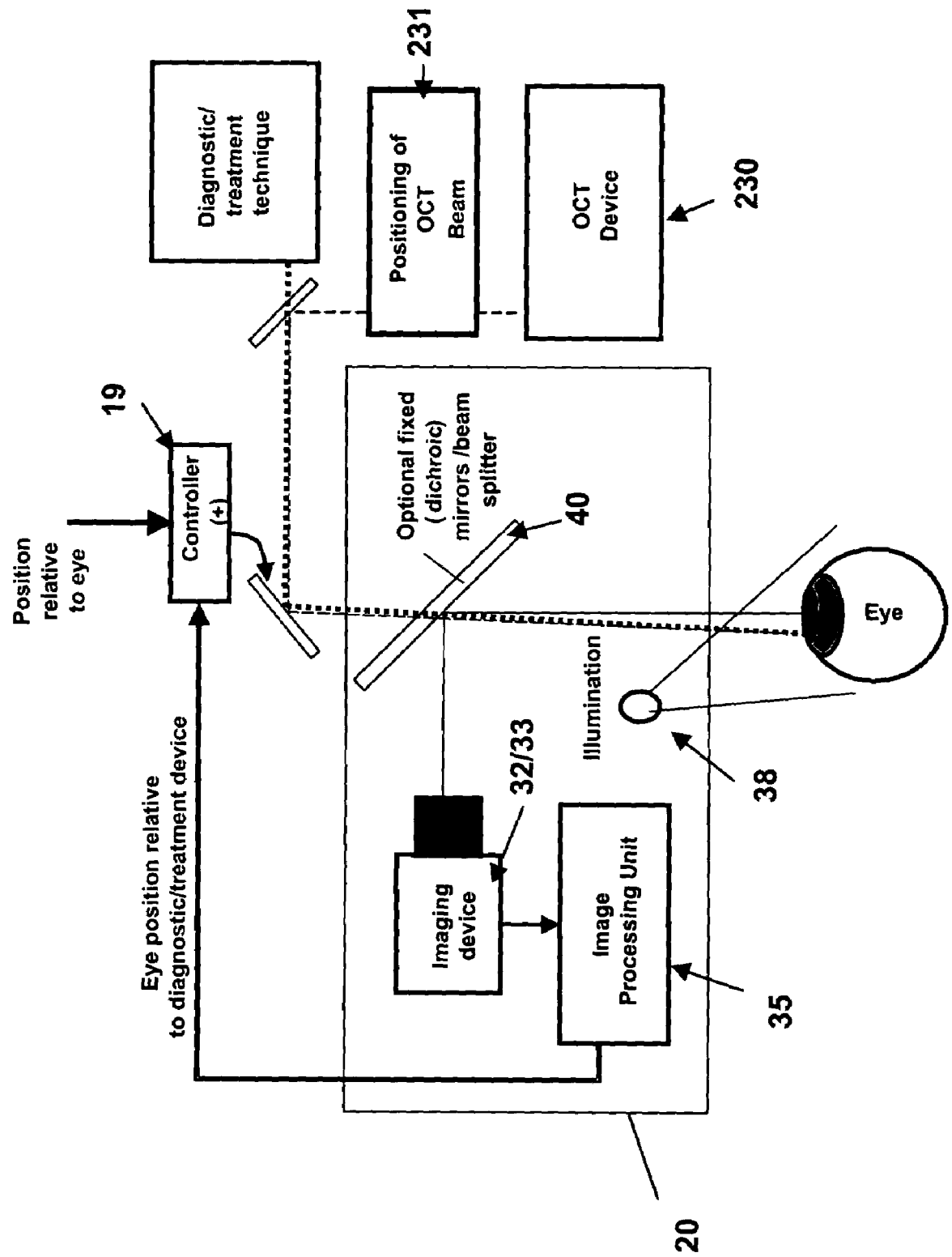
FIG. 23 is a block diagram of the integration of a non-image based measurement system with a video eye tracker.

The Multidimensional Eye Position Measurement Subsystem described in FIG. 3 can optionally be extended with additional non-imaging devices to provide very precise depth measurement. Precision in the order of 10 μm can be obtained using for example the OCT technique. As shown in FIG. 23, the OCT device 230 can be integrated coaxially with the diagnostic and treatment device and optionally positioned relative to the main diagnostic or treatment axis using an additional position device. In case of coaxial alignment of the OCT measurement beam with the treatment device axis, a distance measurements of of the cornea or retina at the treatment location can be obtained relative to the treatment device. Furthermore OCT provides the possibility of measuring the thickness of the cornea at this position. The measurements from imaging devices 32 & 33 and the OCT are preferably synchronized, so that the measurement of the OCT is taken as close as possible if not simultaneously to the measurement of the eye position. Depending on the application, either the eye position from the system 35 is used to control the OCT measurement beam or the eye position is just used to determine the measurement position on the eye in eye coordinates without further adjustments.

The depth and thickness measurements obtained can be used in femto-second laser applications to control the focus of the laser within the cornea. as well as for in corneal thickness measurements for diagnosis or online diagnosis during treatment. If simultaneously multiple point measurements are possible, improved accuracy on rotation measurements—based on the method described in FIG. 20—and foreign object detection—based on the method described in FIG. 22—may be obtained.

Figure 24:
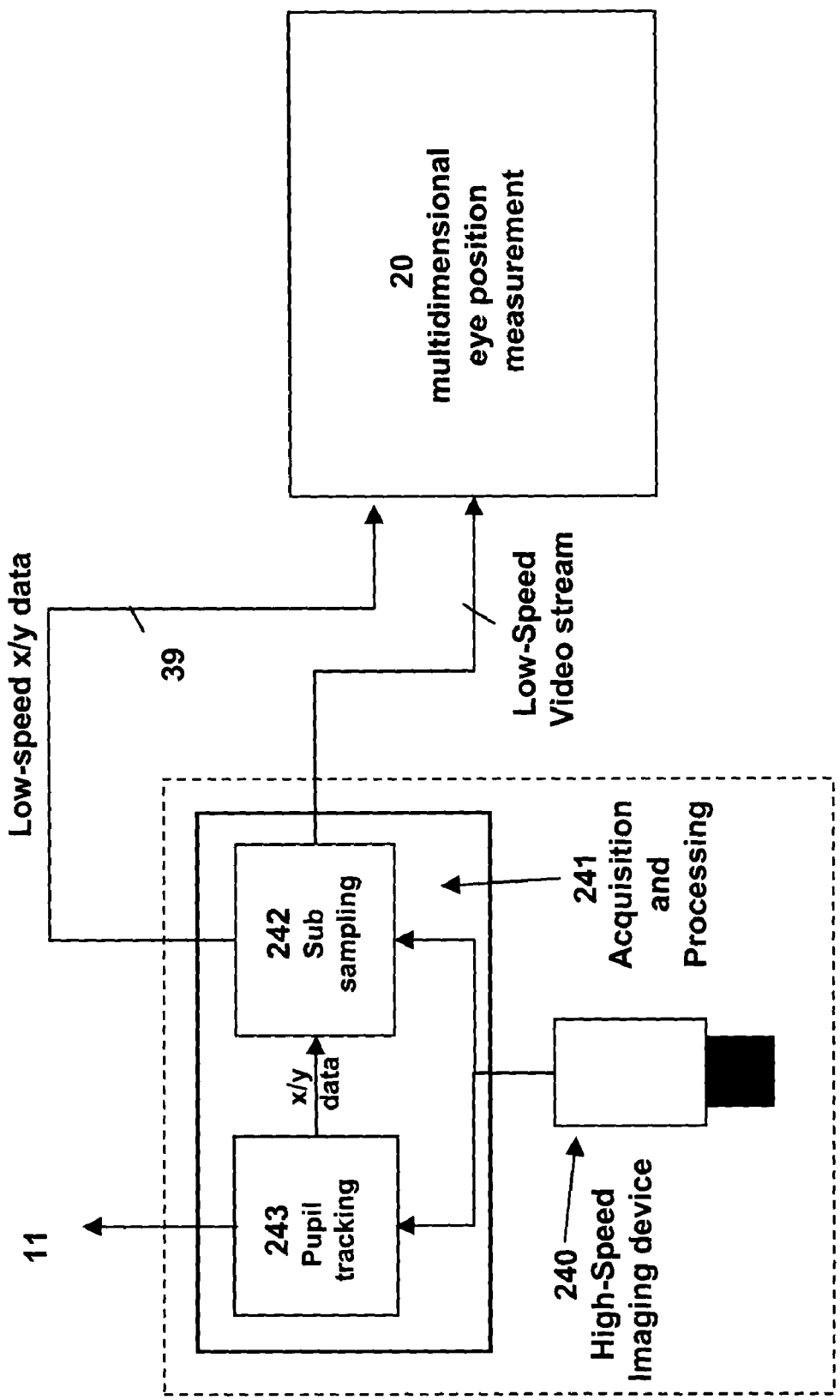
FIG. 24 shows a single high speed camera can be used for both high speed eye tracking and low speed multidimensional eye position measurement.

2 Integration with High Speed Tracking Systems 2.1 High Speed Imaging Device System and Integration In one possible embodiment, the high-speed x/y tracking system consists of a single high speed imaging device 240 which provides an image rate of 200 Hz or more and an acquisition-processing module 241, as shown in FIG. 24. In the preferred embodiment center of the pupil is tracked using a high contrast infrared image providing a clear differentiated pupil for robust detection of the pupil area using thresholding techniques. Other fast implement-able tracking functions using other features of the eye may be used as an alternative. The tracking function of the high speed images are performed on high speed image processing system in module 243.

The integration with the low-speed measurement system may be performed by the device 242. This device subsamples the x/y position data coming from 243 as well as the digital video stream. The sub-sampling is performed to match processing rate of the lower speed Eye Position Measurement Subsystem 20. For example, if imaging device 240 has a frame rate of 250 Hz, a sub-sampling by factor 5 will produce an output at 50 Hz for feeding a lower speed Eye Position Measurement Subsystem with 50 Hz. The sub-sampled video stream can be used in order to replace one of the imaging sensors of system 20 and therefore reducing the complexity and cost of system (number of imaging sensors). For example, if imaging device 240 is an on-axis imaging device, the sub-sampled video output may replace the imaging device 32. Alternatively, if 240 is an off-axis imaging device it can replace one of the imaging devices 33. The sub-sampled x/y position of the high speed pupil tracking is provided also to the Eye Position Measurement Subsystem as reference for pupil center shift calculations.

2.2 1 Imaging Device—Very Fast x/y Motion Sensing and Measurement by Selective Line Readout Furthermore, by use of a specific acquisition/processing techniques, the processing time for the high speed tracking can be significantly improved.

Figure 25:
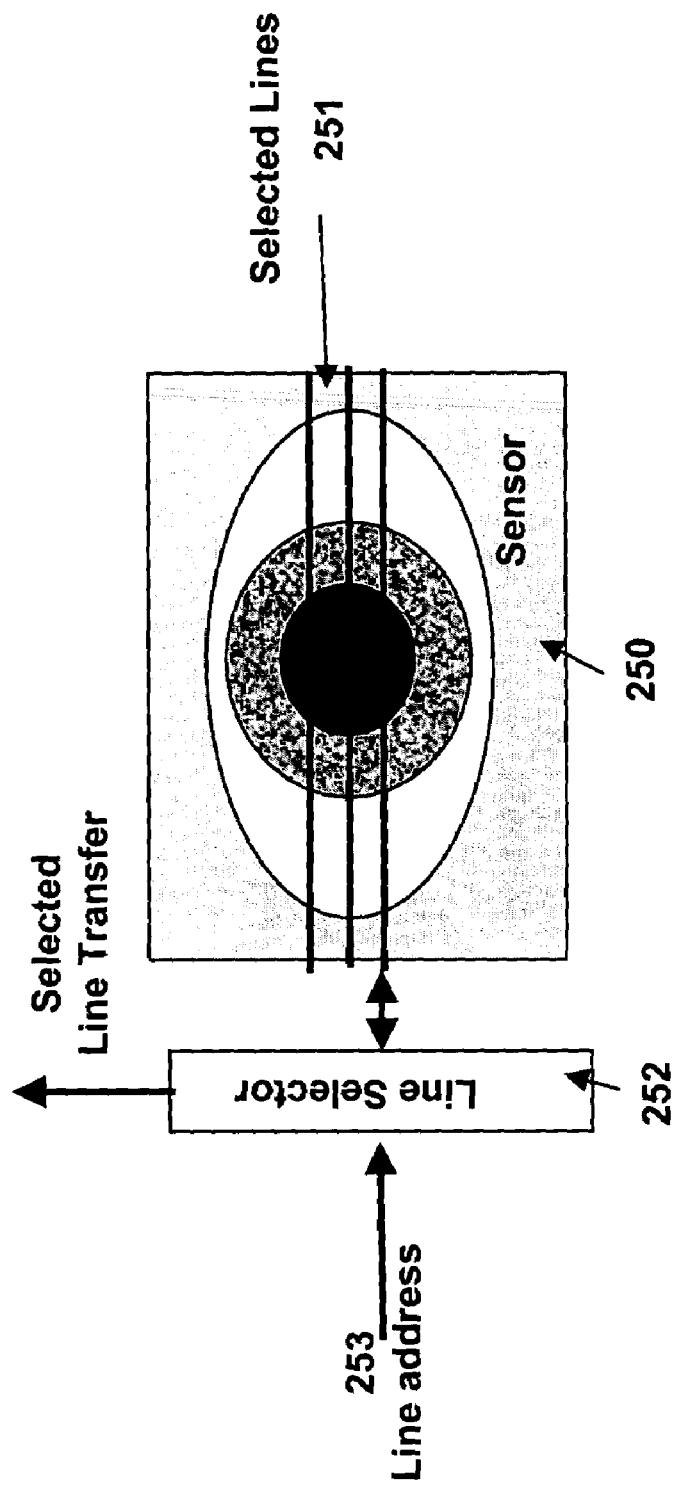
FIG. 25 shows the concept for low latency motion detection using selective line readout for a single high-speed camera

Referring to FIG. 25, certain imaging device sensors 250 allow an individual addressing 253 and reading (via a line selector 252) of lines of the image with and without clearing the information in these lines. Some also allow continuing integration of light intensity after readout.

The selected line readout may be implemented in such a way, that the residual lines of the sensor may be integrated and transferred and processed normally. Thus, image acquisition of the full images of all imaging devices may not be affected; therefore full height and tilt measurement is based on the full image with high spatial resolution. In this way, the means for high speed eye tracking and the means for eye position measurement can be implemented in the same imaging device.

Figure 26:
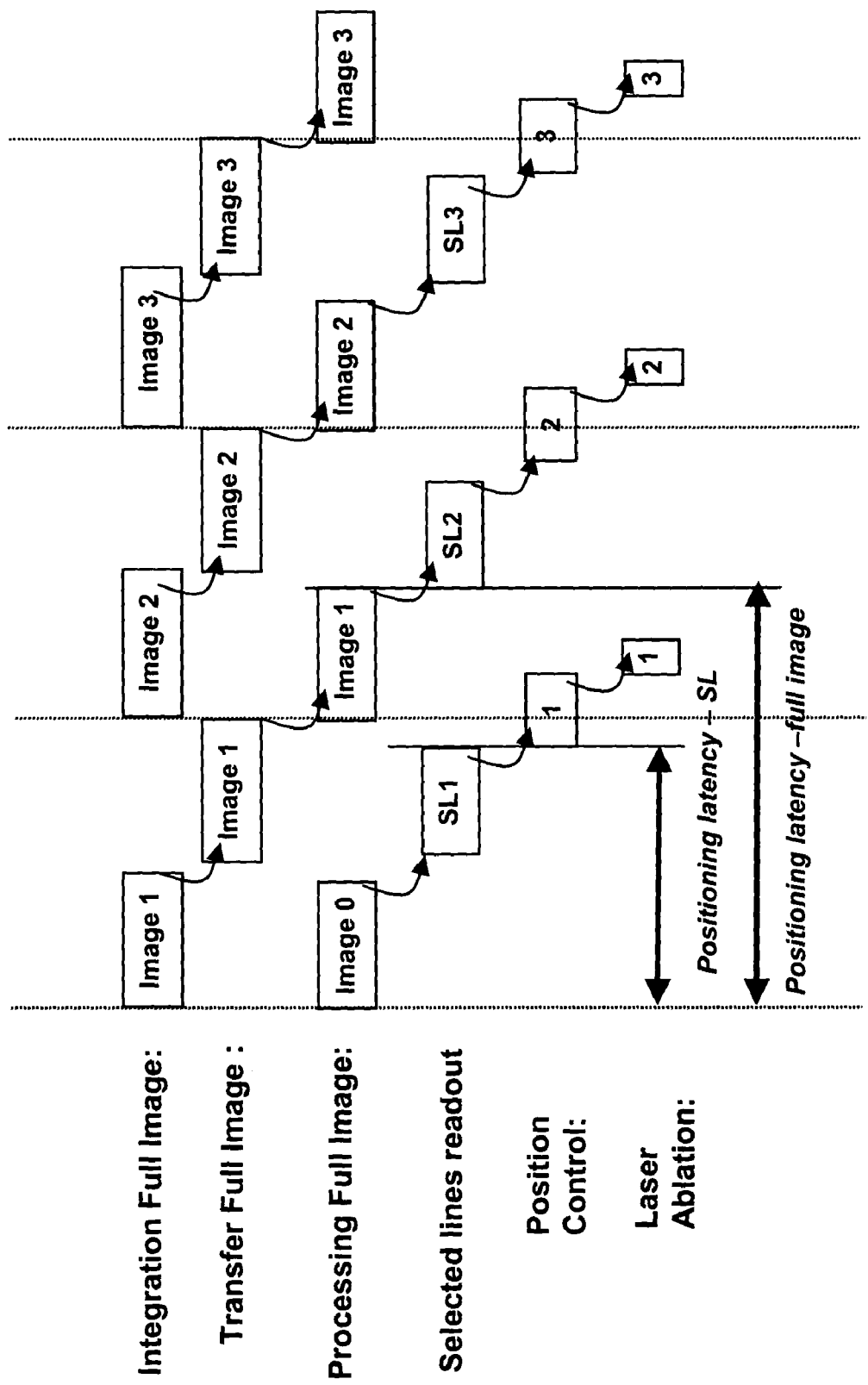
FIG. 26 is a timing diagram of the latency reductions using motion detection with selected line readout, for a single high-speed camera.

With such a subset of lines, a fast position measurement can be realized. The timing diagram illustrating this process is described below and shown in FIG. 26.

The entire image sensor 250 is first illuminated for a short period of time so that the lines are integrating the light intensity 'integration (1)'. The lines are then transferred to the image processing system. The transfer time of the full image is illustrated as 'transfer full image (1)'. The order in which the lines are transferred is modified in such way that first the selected lines SL1 are transferred. While the rest of the image is transferred, the set of selected lines SL1 is processed. The result can be used to position the laser Position Control 1. Since the transfer and processing time of the selected lines is very small, the overall latency 'Position latency —SL' is also small. After the transfer of full image is completed, the full image processing can take place.

The full image processing has the role to establish the future set of selected lines, SL2. The choice is made, for example, by picking up the lines with the highest probability to be located on the tracked landmark (e.g. close to the- of the landmark)

2.3 Multiple Imaging Device—Very Fast x/y Motion Sensing and Measurement by Selective Line Readout Another enhanced high-speed eye tracker consists of a one or multiple additional off-axis imaging devices, as shown in FIG. 15 and FIG. 16, which support the selective line readout technique described before.

Figure 27:
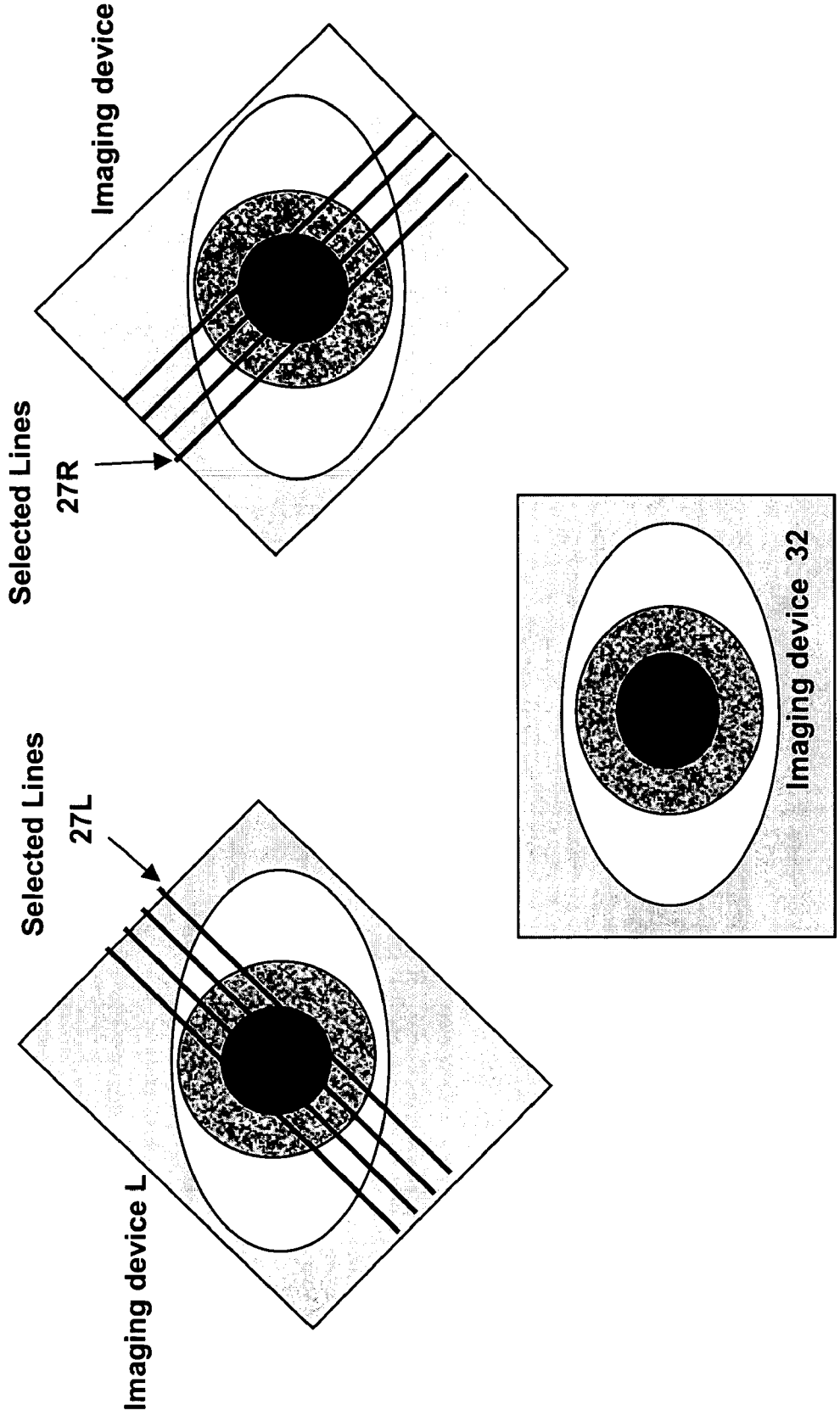
FIG. 27 shows the concept for low latency motion detection using selective line readout and multiple cameras.
Figure 28:
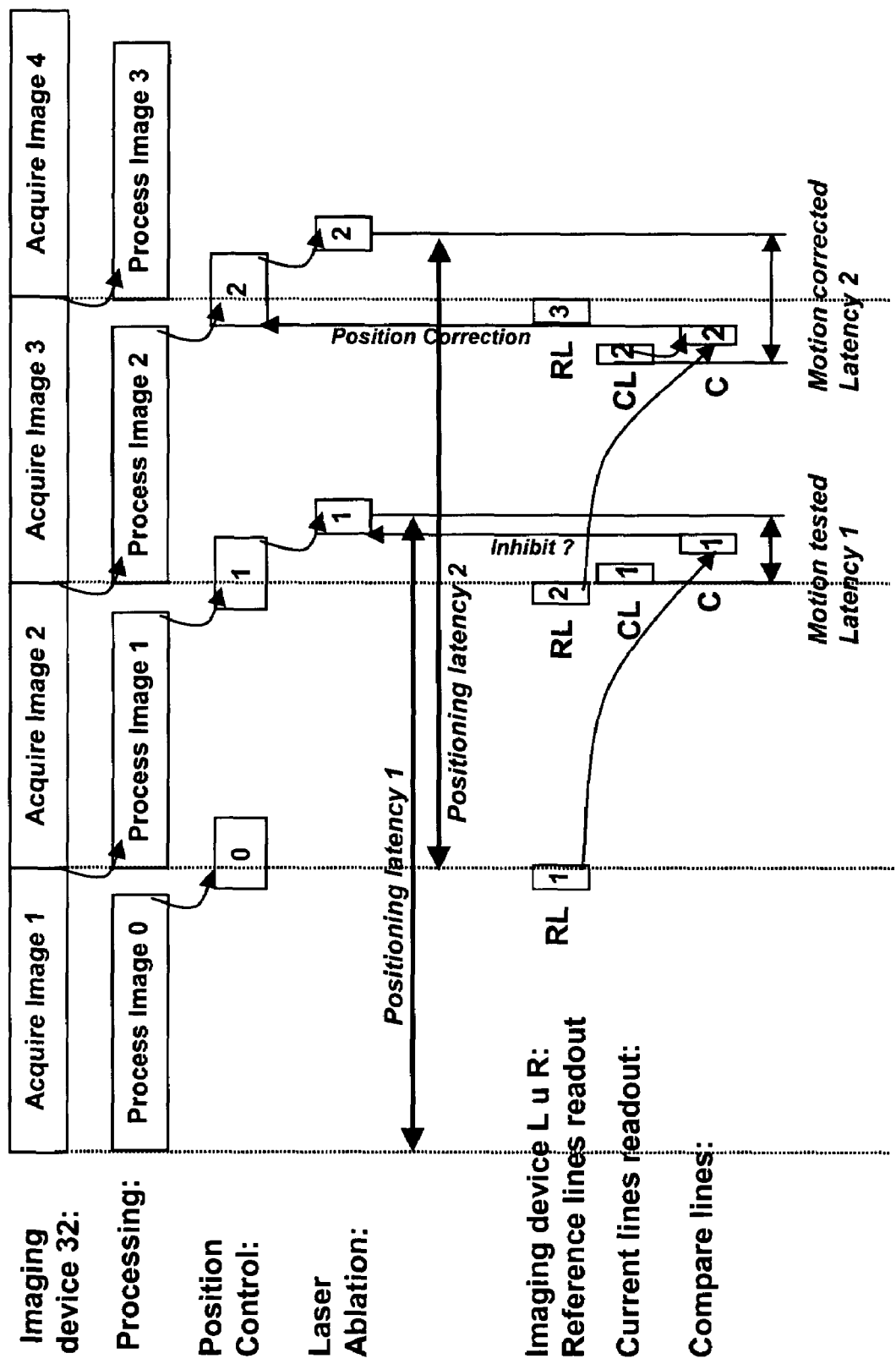
FIG. 28 is a timing diagram of the latency reductions using motion detection with selected line readout, for a multiple cameras.

The specific line readout functionality may be used for imaging devices L and R, as shown in FIG. 27, and may also be used for imaging device 32. The location of the selected subset of lines or area is preferably determined from the location of the tracked landmarks in the previous image of imaging device 32. The timing diagram is shown in FIG. 28.

A full image (1) is acquired with the sensor 32 over the integration period "Acquire Image 1". Within the sensors L and R, at the end of the aquisition of Image 1, these lines are cleared and then the lines integrate the light intensity for only a short time (for example 0.5 ms). The intensity information in these lines RL1 can be transferred quickly (for example 0.2 ms) and stored as reference data for later comparison.

Thereafter the lines from the full image (1) can be transferred and processed while a new image is acquired (2). The full image (1) of sensor 32 is transferred and processed "process image 1". At the end of processing the position data is transferred to control the scanner position. The delay between the start of the image integration and the laser ablation would be "Positioning Latency 1".

Within sensors L and R, slightly before the ablation, the same selected lines 27L, 27R are cleared and reintegrated for a short period CL1. The information from these current lines, CL1, is transferred and compared by C1 to the reference lines RL1.

If a significant change of the information between the reference lines RL1 and current lines CL1 occurred, the ablation laser shot will be inhibited to protect larger positioning errors.

Furthermore, the difference information between reference lines and current lines may also be used to compensate the position obtained from the full frame processing. In this case, the current lines CL2 and the comparison step C2, are placed before the positioning control event, in order to allow the "Positioning Correction" signal to be used. Since the time for processing and position control is short, the range of eye movement occurred is small enough to be corrected as shown in FIG. 28 as "Motion Corrected Latency 2", which is significantly less than "Positioning Latency 1".

Since readout and processing of only a few video lines consumes only a small amount of time (say 0.5 ms), very fast eye movements can be captured. Compared to the time of a system using the imaging device in usual mode, the method and system described can be couple of times faster.

The selected line readout may be implemented in such a way, that the residual lines of the sensor may be integrated and transferred and processed normally. Thus, image acquisition of the full images of all imaging devices may not be affected; therefore full height and tilt measurement is based on the full image with high spatial resolution. In this way, the means for high speed eye tracking and the means for eye position measurement can be implemented in the same imaging device.

Using the 3 imaging device system as a support for the selective line readout technique, presents the advantage that higher accuracy can be obtained in position measurement by specializing each of the L and R imaging devices to measure a specific dimension (x or y) of the movement.

Best results are achieved, if the corresponding video lines of each imaging device are perpendicular for imaging device L and R in the image plane (plane of the eye). In this case the spatial resolution is best for movements in horizontal and vertical direction.

The method may be preferably used with the eye imaging device system described above, but may be used also on other eye tracking system configurations (i.e. one or two imaging device configurations) and also other applications where low latency position measurement is required.

Figure 29:
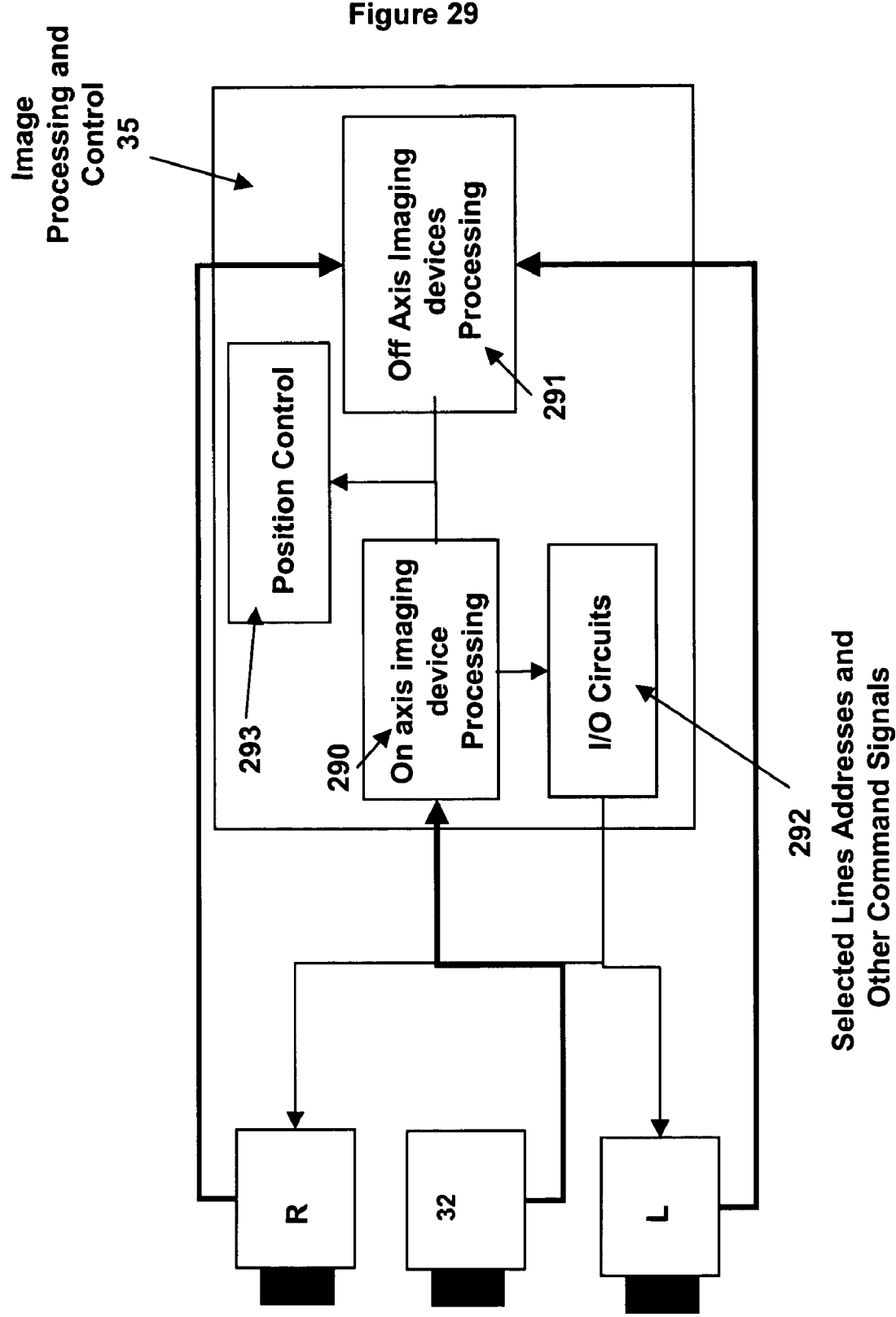
FIG. 29 is a block diagram detailing the image processing and control for the low latency motion detection for multiple cameras.

In a preferred embodiment, the method is used with the 3 eye imaging device system described above. The video lines of imaging devices L and R are perpendicular. Referring to FIG. 29, the image obtained from imaging device 32 is processed by the processing module 290, which computes the position of tracked landmark (for example the center of the pupil), and based on this position computes the subset of lines 27L and 27R that will be read from the imaging devices L and R. As example, the lines 27L and 27R may be chosen to be the closest lines to the landmark center position. The position of lines 27L and 27R are transmitted to an I/O circuit 292, which transforms them in digital lines addresses for the imaging devices L and R. The I/O circuit also transmits the synchronization signals for the imaging devices and possibly other command signals like zoom/focus/position if necessary. Alternatively the synchronization/commands signals for imaging devices L and R can be provided directly by imaging device 32 that than acts like a master imaging device.

The image data from imaging devices L and R are then transferred to the processing module 291. Module 291 computes the motion registered by the selected lines 27R, 27L. The data is transmitted to module 293 together with the position measured by module 290. The module 293 finally combines the two data and outputs the position control and/or laser inhibit signal.

Figure 30:
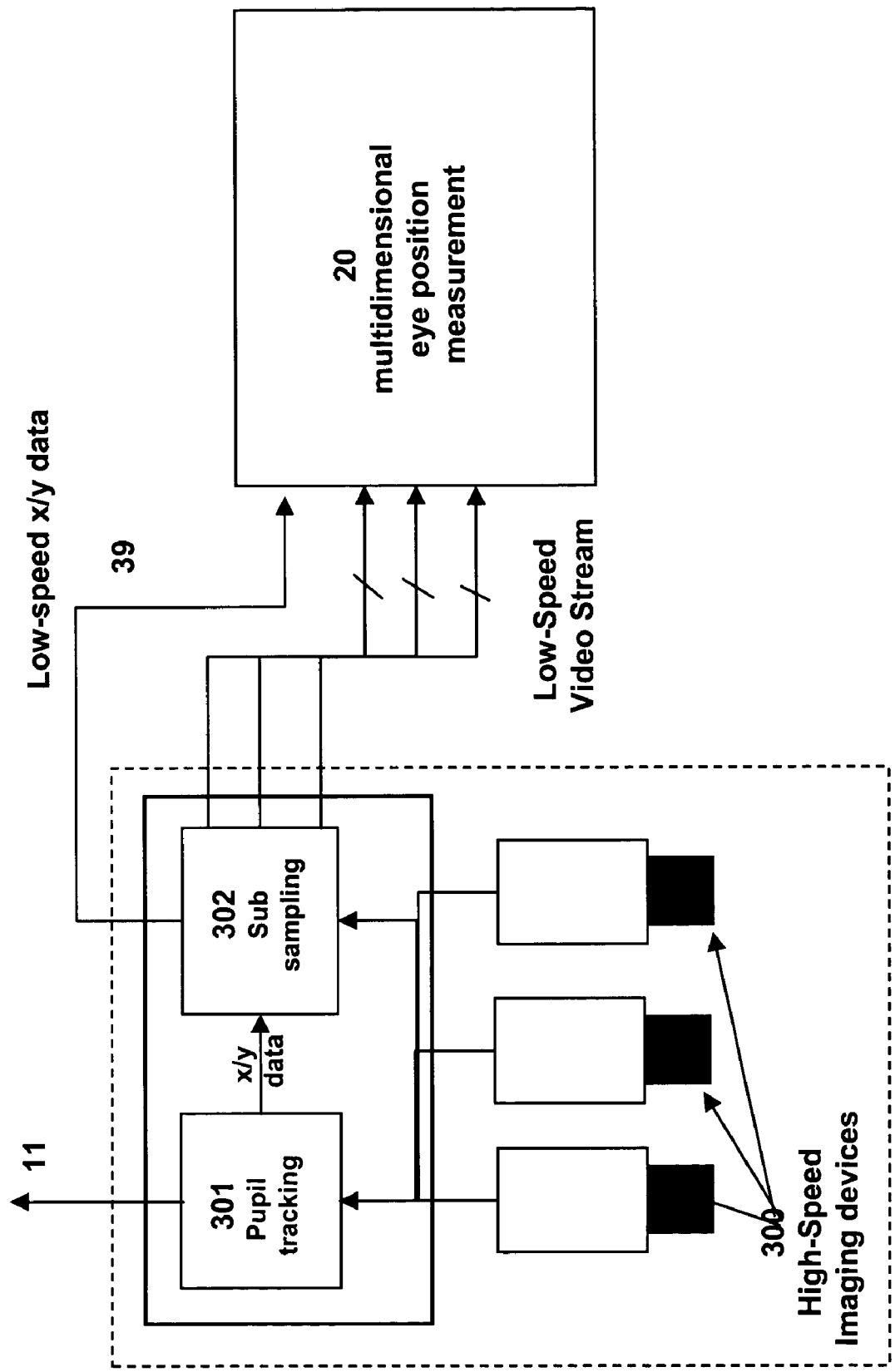
FIG. 30 shows how the multiple high speed cameras used for the high speed tracking, could also provide the video stream and required x, y data for the low speed multi-dimensional eye position measurement system.

The integration of the High Speed Tracking X/Y tracking system using multiple high speed imaging devices with the Multidimensional Eye Position Measurement System is presented in FIG. 30. Using a similar concept as for the single high-speed imaging device integration shown in FIG. 24, the sub-sampling module 302 produces 3 video streams and one x/y data stream at the rate of the low-speed system. Any one of the video streams as well as any combination of them, can be used to replace partially or completely the imaging devices of the low-speed system, namely modules 32 and/or 33.

2.4 Integration with LADAR Tracker

Non-imaging based tracking systems, such as laser based, linear array based, or photodiode based tracking techniques can provide very high sampling rates, low latency in x/y tracking and consequently high dynamic positioning accuracy during fast eye movements.

In another embodiment this invention proposes therefore the integration of a non-image based fast tracking system, hereafter in a specific example using the LADAR tracker, as the high speed tracking system used in combination with the Eye Position Measurement System to create the Eye Monitor.

Figure 31:
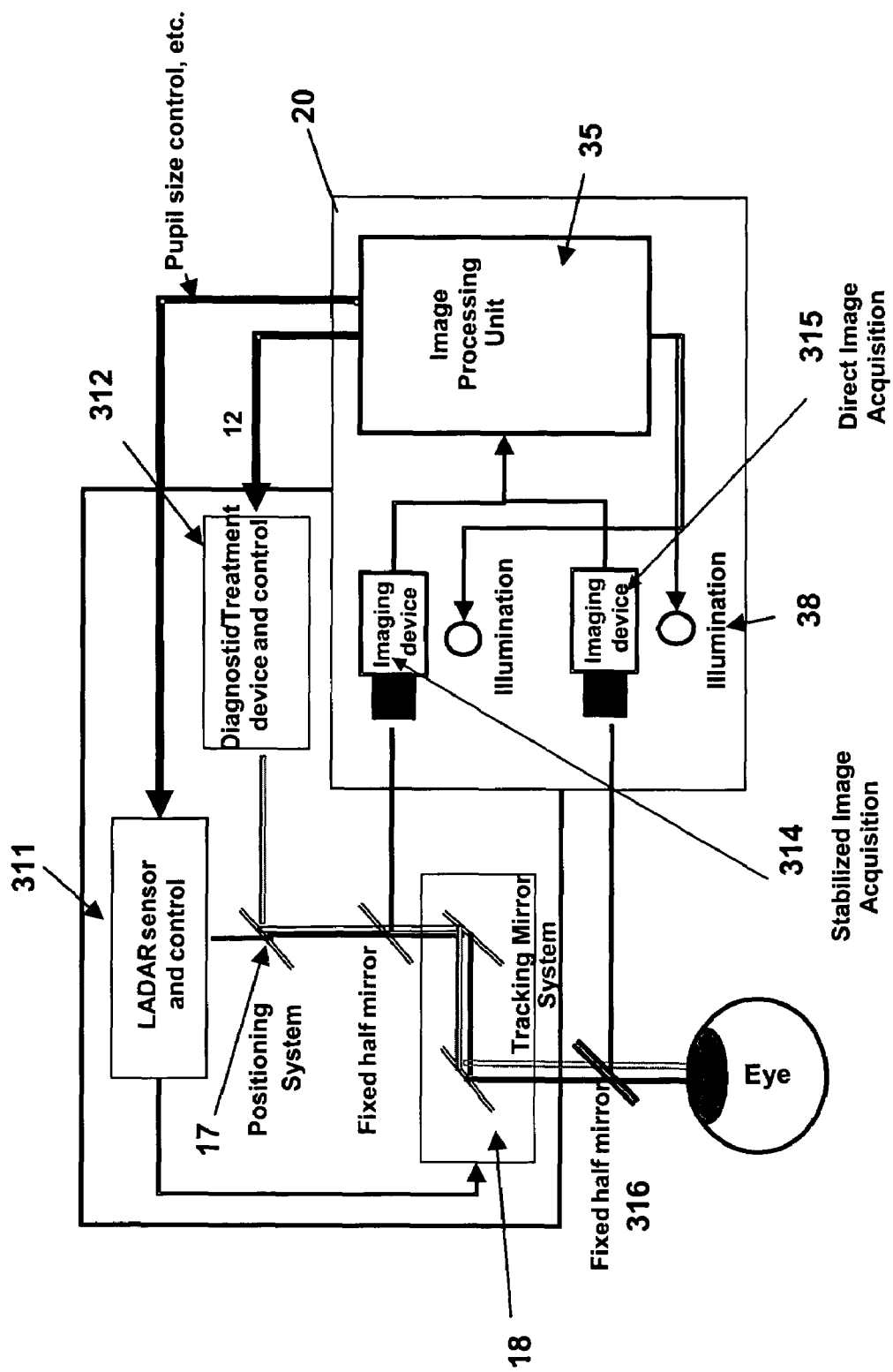
FIG. 31 is a block diagram of the integration of multiple cameras with a non-image based tracker such as the LADAR tracker. One camera views the stabilized image of the eye, while another camera system directly views the eye.

Integration of the imaging based eye tracking with the LADAR Tracker is shown in FIG. 31. The imaging device of the Multidimensional Eye Position Measurement System can be integrated in two locations: 314 and/or 315. In the stabilized position 314, the sensor is viewing the eye via the tracking mirror 18. Since this viewing is always aligned with the optical axes of treatment 312, the on axis imaging device 32 can be placed in this position.

In device fixed position 315, the sensors are either viewing the eye either directly, or via a fixed mirror 316. Depending on the position of this mirror the viewing angle can be adjusted. Therefore the module 315 can contain either the sensor 32 coaxial with the optical axes of treatment 312, or the sensors 33 tilted against the optical axes, or a combination of both.

In a preferred embodiment the imaging device 32 is placed in position 314, while the imaging device 33 may be placed in position 315.

The LADAR tracker stabilizes fast x/y eye movements via the tracking mirror 18, providing an almost "still" image to sensor 314 and also centered on the pupil position. This offers significant advantages in terms of image processing complexity. The computation time is drastically reduced by optimized areas of interest. Since the analyzed features—limbus, blood vessels, iris—appear limited in range of movement, the search ranges can be much smaller. Also the exposure time of the sensor can be increased without alterations caused by the motion blur effects since the main eye movement is already compensated for. Only small offsets due to pupil center shift have to be determined and provided to the LADAR control unit. The image based tracker can identify any shift of pupil size independent features in the image and therefore provide a corrective information to the diagnostic or treatment device to compensate the movements which are not compensated with the LADAR tracker.

During initialization of the tracking the imaging based Eye Position Measurement System provides information such as pupil diameter and position of the pupil-iris boundary to adjust the position and relative location of the spots of the LADAR tracker. Pupil size changes measured continuously with the image based Eye Position Measurement System allow continuous adjustment of the LADAR tracker spot distance hence being able to track on the pupil iris boundary with varying pupil sizes. a major limitation of the LADAR tracker—currently resolved by the pupil dilation requirement which could be removed with the imaging based tracker.

Optionally the reflection of the LADAR tracker spots may be registered with the Eye Position Measurement System to allow calibration of both tracking systems.

This Integration therefore combines the benefits of the fast LADAR tracker to track fast saccades with the benefits of video-based Multidimensional Eye Position Measurement System. Pupil size and pupil center shift determination and compensation provided by Multidimensional Eye Position Measurement System allows the LADAR tracker to track fast and accurate even with varying in pupil sizes. Measurement of other degrees of eye movements with the Multidimensional Eye Position Measurement System can be corrected with the laser positioning device of the LADAR tracker. This integration also provides the advantage to be automated, more accurate, robust and reliable (eye position is determined twice).

2.5 Integration with CRP Tracker

Similar as with the LADAR tracker (replace LADAR sensor and control unit 311, with CRP/sensor and control in FIG. 31), the image based tracker may be integrated with other closed loop tracking systems as the CRP. Instead of CRP also other tracking techniques may be used by replacing the LADAR sensor and control unit 311 with the alternative solution.

In this configuration the image based tracking provides measurement of the absolute orientation of the eye relative to the diagnostic and treatment device and provides means for automatic identification of the specific area used on the object surface which the CRP tracker is using for tracking to lock on (i.e. area on the retina or area on the iris or blood vessels on the sclera). After the CRP tracker has locked onto this feature, relative horizontal and vertical movements are compensated at high speed and the image of the eye may be obtained stabilized through the CRP tracking mirrors.

This stabilized image may thus be used by the described image based tracking system to provide all above described measurements and functions.

3 Overall Laser System and Eye Tracker Calibration Technique

For absolute positioning accuracy, the coordinate system of the Eye Tracking System has to be aligned and calibrated with the coordinate system of the laser treatment system.

This kind of calibration is currently performed manually, calibrating each process step separately. Therefore, calibration errors for each individual process step are often significant and the sum of errors of each calibrations step may be significant. Furthermore, manual calibrations may include "subjective" errors or require a certain time and therefore may be done not very frequently.

Figure 32:
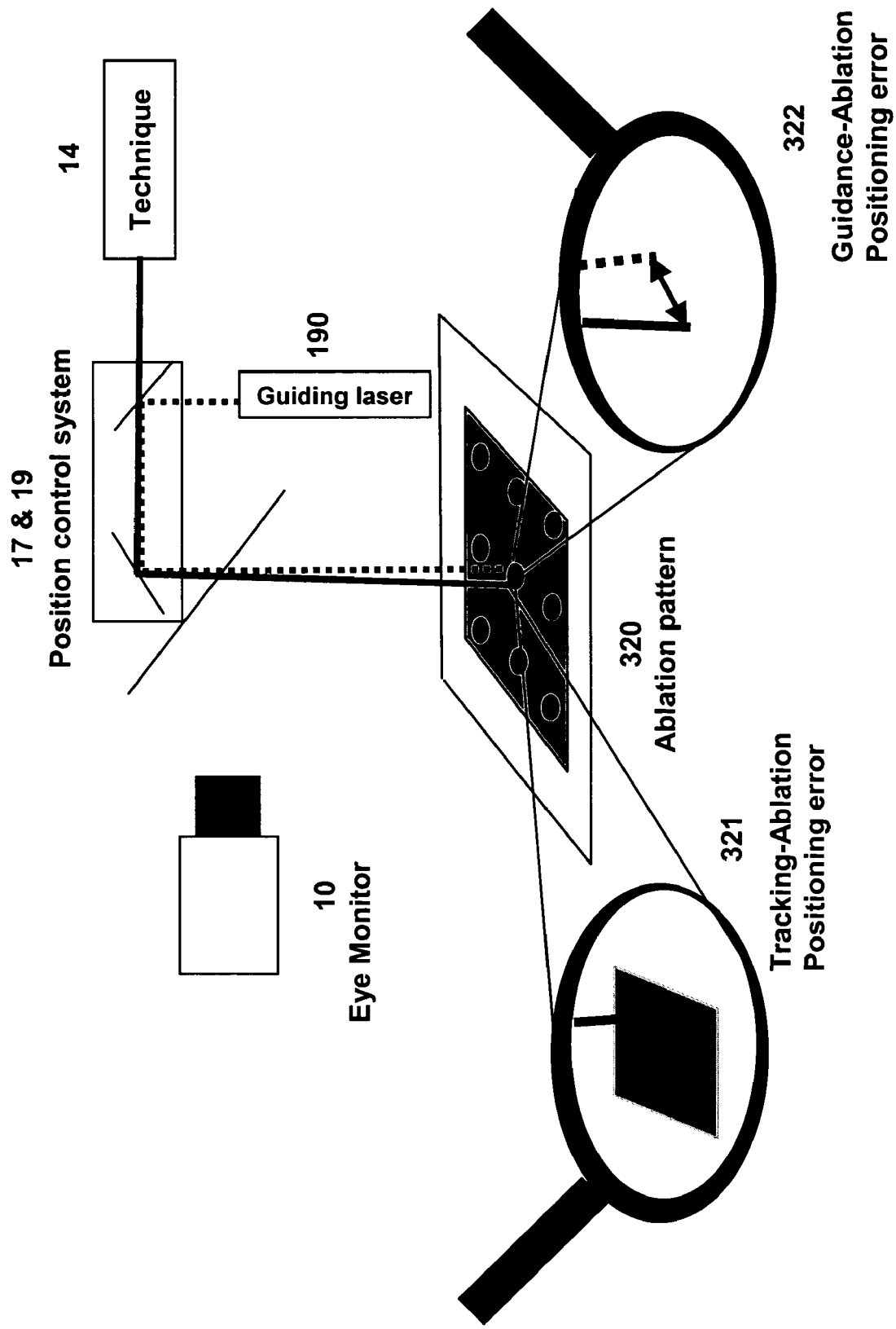
FIG. 32 illustrates an improved technique for calibrating a laser using a guidance laser.

For this reason and integrated calibration procedure calibration the overall system with its own measurement devices, i.e. the eye tracking system is proposed below. See FIG. 32 for a detailed illustration.

1. Fix grey ablation square/pattern 93 with white frame underneath laser in surgery plane so it is completely visible within the field of view of the eye monitor device 10. It is best to use a square with different length and width to allow also identification of orientation of the square
2. Obtain image from eye tracking imaging device of the square and measure by image processing the length and width of this square and orientation in eye tracking coordinates
3. Compute aspect ratio of the imaging system from known width and height of the calibration square.
4. Obtain calibration of imaging coordinate system (pixels) into physical coordinate system (µm) by the known size of the square.
5. Perform specific ablation pattern with 4 or more separate targets within the square at known scanner settings. The ablation pattern is designed in such a way that an ablation on the ablation patterns changes significantly the brightness at that location.
6. Alternatively or additionally, if a guiding laser is used, the reflection of the guiding laser position is acquired with the eye tracking device on the ablation pattern before each ablation spot is created.
7. The centre position for each ablated spot is measured with the eye tracking device.
8. Comparing the created positions of the ablation targets obtained from the eye tracking device (by means of image processing) with the position data provided to the position control system as in detail 321, the position control system can be calibrated in physical coordinates and into the eye tracking coordinates. This allows calculation of gain, offset for x and y axis as well as possible rotation of the scanning system in the eye tracking coordinate system.

9. Comparing the ablation target positions with the positions obtained from the reflection of the guiding laser as in detail 322 (see step 6) a possible misalignment of the ablation and guiding laser can be measured and compensated for correct feedback control.

We claim:

1. A System for determining the orientation of the eye consisting of the following sub-systems:
    an x, y high-speed eye tracking system, for measuring the very fast translation or saccadic motion of the eye, relative to an ophthalmic surgical, diagnostic or treatment device or instrument;
    a second position measurement system for measuring slower eye movements, such as multiple dimensions of eye position and / or position of eye parts, relative to an ophthalmic surgical, diagnostic or treatment device or instrument; and
    a system for combining the measurements of the two previous systems for obtaining a multiple dimensional model of the eye position that is more accurate than the model obtainable from either system individually; wherein the x, y eye tracking system is either a multiple imaging device solution in which one imaging device is coaxial to the eye and either one or two off-axis imaging devices using selective line readout, or a single high speed imaging device using selective line readout, said system comprising
        an imaging device sensor configured to individually address and read a set of selected lines;
        a processing device for processing data which has been transferred from said imaging device sensor to said processing device; and
        a laser treatment device the position of which is controlled by a laser position control, wherein, while the rest of the image is being transferred, the set of selected lines which has already been transferred is processed to obtain a processing result which is used to position the laser position control of said laser treatment device, and wherein after the image has been fully transferred to a processing device, the full image is processed in order to establish a future set of selected lines based on a tracked landmark.

2. The system according to claim 1, wherein the second eye position measurement system is a single coaxial imaging device or multiple imaging devices for measuring the eye, or a non-image based depth measurement system.

3. The system according to claim 1, where the system for combining the measurements obtains the multiple dimensional model of the eye position in order to calibrate one or both of the eye tracking devices, such as set the region of interest, spot location, or scanning limits for the other eye location device; or to provide 3 or more dimensions of eye position.

4. The system according to claim 1, which includes a structured illumination and according filtering means to improve visibility of a unique combination of trackable features.

5. The system of claim 1, said system comprising.
    a means for making a reference measurement of three or more points on the eye, in three dimensions;
    a means for measuring these same reference points at a subsequent time in three dimensions; and
    a means for determining the position of the eye from the change in position at these multiple points.

6. The system of claim 1, said system comprising:
    a means for tracking the translational eye position;
    a means for tracking the translational head position; and
    a means for determining the rotation of the eye from the variation of difference between head position and eye position.

7. A use of the system according to claim 1, for the purpose of laser refractive surgery in order to intra-operatively update the pre-programmed shot pattern on the basis of the determined orientation of the eye to correct for eye position and its effect on correction efficacy.

8. The system of claim 1, wherein the lines used for selective line readout are selected by picking up the lines with the highest probability to be located on the tracked landmark.

9. A method for determining the orientation of the eye consisting of the following steps:
    tracking eye movement at a tracking rate that is sufficiently fast to follow the saccadic motion of the eye;
    measuring other slower changing positions for the eye or parts of the eye at a slow rate, relative to an ophthalmic surgical, diagnostic or treatment device or instrument;
    combining the measurements of the two previous systems to obtain a multiple dimensional model of the eye position that is more accurate than the model obtainable from either system individually; wherein the step of eye tracking is performed by either multiple imaging devices and the use of selective line readout or by a single imaging device using selective line readout;
    individually addressing and reading out a set of selected lines of an imaging device sensor and transferring them to a processing device for processing;
    while the rest of the image is being transferred, processing the set of selected lines which has already being transferred to obtain a processing result which is used to position the laser position control of said laser treatment device; and
    after the full image has been transferred to a processing device, processing the full image in order to establish the future set of selected lines based on a tracked landmark.

10. The method according to claim 9, where the position measurement of other components of eye movement comprises either detecting foreign objects or compensating for pupil offset or measuring torsion or measuring eye rotation or measuring depth or a combination thereof.

11. The method according to claim 9, which includes structured illuminating and filtering method to improve visibility of a unique combination of trackable features.

12. The method of claim 9, said method comprising:
    making a reference measurement of three or more points on the eye, in three dimensions;
    measuring the same points at a subsequent time in three dimensions; determining the orientation from the eye from the change in position at these multiple points.

13. The method of claim 9, said method comprising:
    measuring the translational eye position;
    measuring the translational head position; and
    determining the rotation of the eye from the variation of difference between head position and eye position.

14. A use of the method according to claim 9, for the purpose of laser refractive surgery in order to intra-operatively update the pre-programmed shot pattern on the basis of the determined orientation of the eye to correct for eye position and its effect on correction efficacy.

15. The method of claim 9, wherein the lines used for selective line readout are selected by picking up the lines with the highest probability to be located on the tracked landmark.

* * * * *

UNITED STATES PATENT AND TRADEMARK OFFICE
CERTIFICATE OF CORRECTION

PATENT NO. : 7,480,396 B2  Page 1 of 1
APPLICATION NO. : 10/630001
DATED : January 20, 2009
INVENTOR(S) : Winfried Teiwes and Horia Grecu It is certified that error appears in the above-identified patent and that said Letters Patent is hereby corrected as shown below:

On the Title Page, Item (73) the Assignee should read: -- Sensomotoric Instruments GmbH --.

Signed and Sealed this

Thirty-first Day of March, 2009

JOHN DOLL
*Acting Director of the United States Patent and Trademark Office*